US012688913B1

(12) United States Patent
Roll et al.

(10) Patent No.: US 12,688,913 B1
(45) Date of Patent: Jul. 21, 2026

(54) SYSTEMS AND METHODS FOR ELECTRONICALLY MONITORING EXPECTED ADVERSE REACTIONS OF PHARMACEUTICAL PRODUCTS

(71) Applicant: Veeva Systems Inc., Pleasanton, CA (US)

(72) Inventors: Asaf Roll, Richmond Hill (CA); Ying Zhuo Wang, Toronto (CA); Justin Yuping Lai, Markham (CA)

(73) Assignee: Veeva Systems Inc., Pleasanton, CA (US)

( * ) Notice: Subject to any disclaimer, the term of this patent is extended or adjusted under 35 U.S.C. 154(b) by 158 days.

(21) Appl. No.: 18/155,873

(22) Filed: Jan. 18, 2023

Related U.S. Application Data

(63) Continuation of application No. 17/691,751, filed on Mar. 10, 2022, now Pat. No. 12,347,536.

(60) Provisional application No. 63/263,503, filed on Nov. 3, 2021.

(51) Int. Cl.
*G16H 15/00* (2018.01)
*G16H 40/67* (2018.01)
*G16H 70/40* (2018.01)

(52) U.S. Cl.
CPC ............. *G16H 15/00* (2018.01); *G16H 40/67* (2018.01); *G16H 70/40* (2018.01)

(58) Field of Classification Search
None
See application file for complete search history.

(56) References Cited

U.S. PATENT DOCUMENTS

| | | | | |
|---|---|---|---|---|
| 2015/0356646 A1* | 12/2015 | Spitznagel | ............. | G16H 40/20 705/2 |
| 2018/0373844 A1* | 12/2018 | Ferrandez-Escamez | .................... | G16H 50/20 |
| 2020/0176093 A1* | 6/2020 | Kuchibotla | ........... | G06F 16/248 |
| 2021/0366609 A1* | 11/2021 | Nabutovsky | ........... | A61B 5/742 |

OTHER PUBLICATIONS

Bousquet et al. ("Appraisal of the MedDRA conceptual structure for describing and grouping adverse drug reactions." Drug Safety 28 (2005): 19-34) (Year: 2005).*

(Continued)

*Primary Examiner* — Christopher B Tokarczyk

(57) ABSTRACT

A method for determining and indicating expectedness of an adverse event. The method includes receiving adverse event data associated with the adverse event. The method further includes determining an electronic reference document associated with the clinical study. The method further includes selecting the electronic reference document including a defined adverse reaction from the document repository. The defined adverse reaction includes an active start date. The method further includes generating a case dataset including at least a portion of the adverse event data. The method further includes determining the expectedness of the adverse event based on the defined adverse reaction of the electronic reference document and the adverse event data. The method further includes determining a submission timeframe associated with the case dataset based on the expectedness of the adverse event.

20 Claims, 10 Drawing Sheets

(56)  References Cited

OTHER PUBLICATIONS

Oracle Argus Safety Administrator's Guide, Release 8.1.2, E93475-01, Feb. 2018.

Oracle Argus Safety, User's Guide, Release 8.1.2, E93471-01, Feb. 2018.

Oracle, "Oracle Argus Safety—User Guide" Oct. 2020, Release 8.2.2, 206 pages printed (Year: 2020).

* cited by examiner

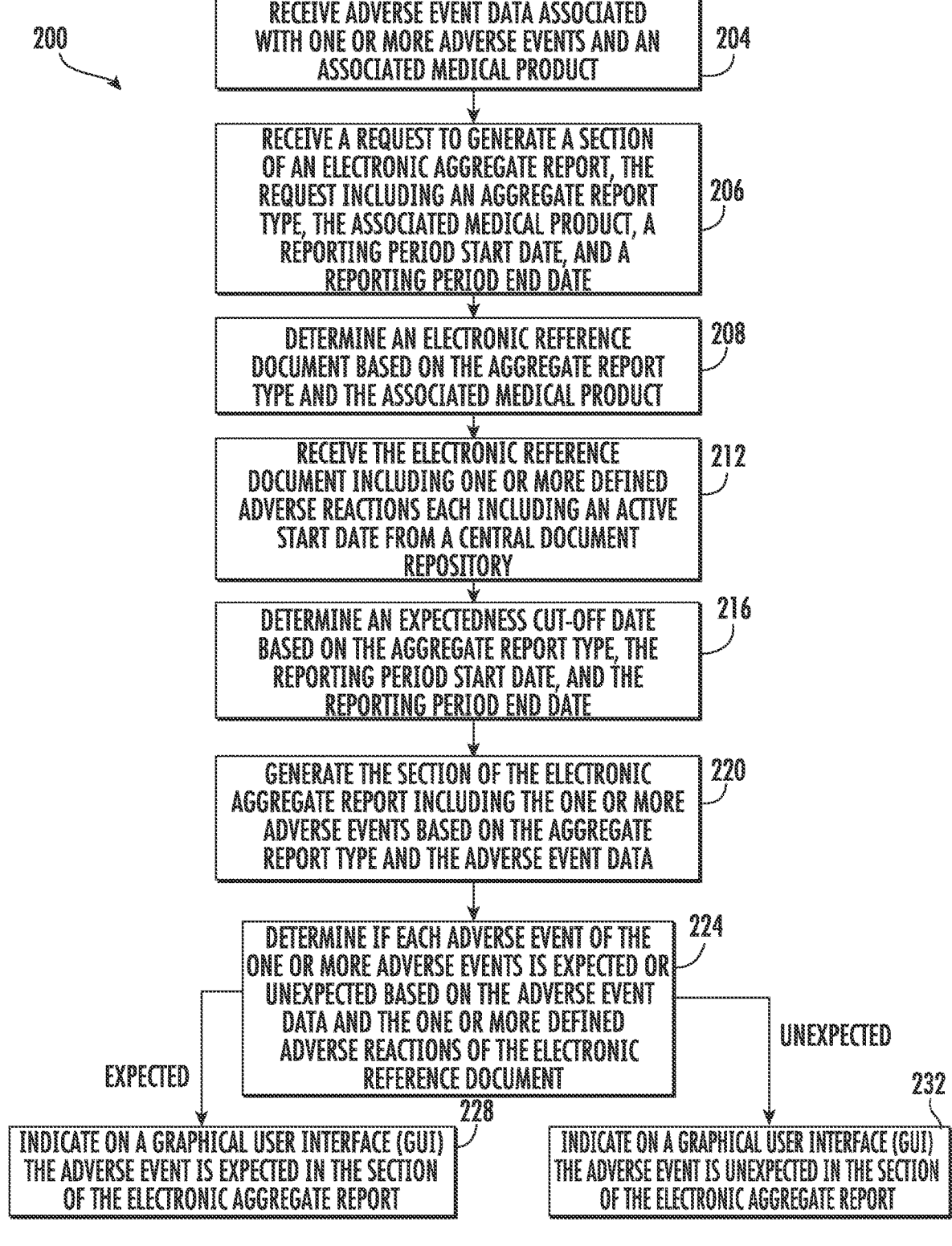

200

204 — RECEIVE ADVERSE EVENT DATA ASSOCIATED WITH ONE OR MORE ADVERSE EVENTS AND AN ASSOCIATED MEDICAL PRODUCT

206 — RECEIVE A REQUEST TO GENERATE A SECTION OF AN ELECTRONIC AGGREGATE REPORT, THE REQUEST INCLUDING AN AGGREGATE REPORT TYPE, THE ASSOCIATED MEDICAL PRODUCT, A REPORTING PERIOD START DATE, AND A REPORTING PERIOD END DATE

208 — DETERMINE AN ELECTRONIC REFERENCE DOCUMENT BASED ON THE AGGREGATE REPORT TYPE AND THE ASSOCIATED MEDICAL PRODUCT

212 — RECEIVE THE ELECTRONIC REFERENCE DOCUMENT INCLUDING ONE OR MORE DEFINED ADVERSE REACTIONS EACH INCLUDING AN ACTIVE START DATE FROM A CENTRAL DOCUMENT REPOSITORY

216 — DETERMINE AN EXPECTEDNESS CUT-OFF DATE BASED ON THE AGGREGATE REPORT TYPE, THE REPORTING PERIOD START DATE, AND THE REPORTING PERIOD END DATE

220 — GENERATE THE SECTION OF THE ELECTRONIC AGGREGATE REPORT INCLUDING THE ONE OR MORE ADVERSE EVENTS BASED ON THE AGGREGATE REPORT TYPE AND THE ADVERSE EVENT DATA

224 — DETERMINE IF EACH ADVERSE EVENT OF THE ONE OR MORE ADVERSE EVENTS IS EXPECTED OR UNEXPECTED BASED ON THE ADVERSE EVENT DATA AND THE ONE OR MORE DEFINED ADVERSE REACTIONS OF THE ELECTRONIC REFERENCE DOCUMENT

EXPECTED

UNEXPECTED

228 — INDICATE ON A GRAPHICAL USER INTERFACE (GUI) THE ADVERSE EVENT IS EXPECTED IN THE SECTION OF THE ELECTRONIC AGGREGATE REPORT

232 — INDICATE ON A GRAPHICAL USER INTERFACE (GUI) THE ADVERSE EVENT IS UNEXPECTED IN THE SECTION OF THE ELECTRONIC AGGREGATE REPORT

FIG. 2

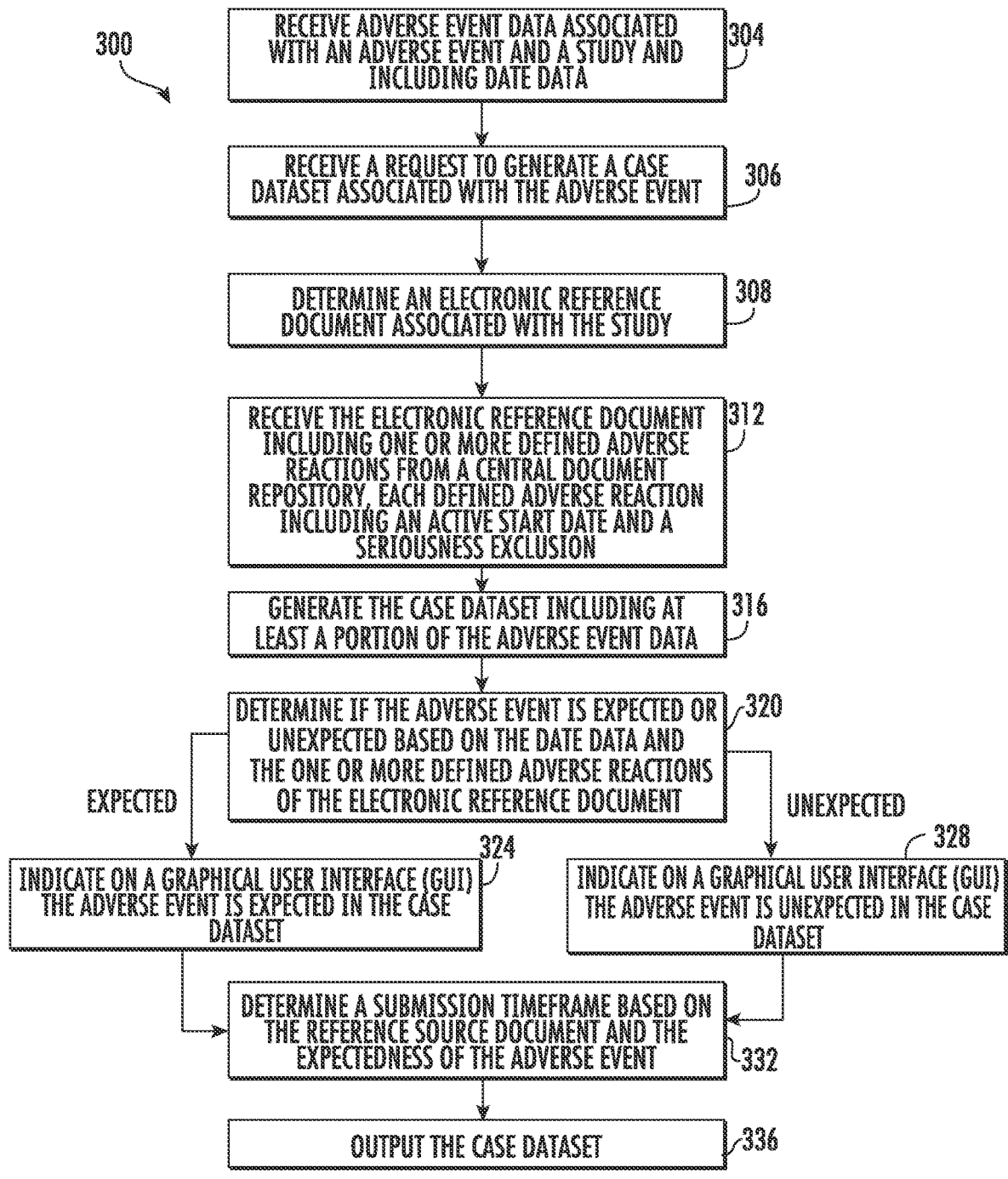

300

RECEIVE ADVERSE EVENT DATA ASSOCIATED WITH AN ADVERSE EVENT AND A STUDY AND INCLUDING DATE DATA — 304

RECEIVE A REQUEST TO GENERATE A CASE DATASET ASSOCIATED WITH THE ADVERSE EVENT — 306

DETERMINE AN ELECTRONIC REFERENCE DOCUMENT ASSOCIATED WITH THE STUDY — 308

RECEIVE THE ELECTRONIC REFERENCE DOCUMENT INCLUDING ONE OR MORE DEFINED ADVERSE REACTIONS FROM A CENTRAL DOCUMENT REPOSITORY, EACH DEFINED ADVERSE REACTION INCLUDING AN ACTIVE START DATE AND A SERIOUSNESS EXCLUSION — 312

GENERATE THE CASE DATASET INCLUDING AT LEAST A PORTION OF THE ADVERSE EVENT DATA — 316

DETERMINE IF THE ADVERSE EVENT IS EXPECTED OR UNEXPECTED BASED ON THE DATE DATA AND THE ONE OR MORE DEFINED ADVERSE REACTIONS OF THE ELECTRONIC REFERENCE DOCUMENT — 320

EXPECTED                    UNEXPECTED

INDICATE ON A GRAPHICAL USER INTERFACE (GUI) THE ADVERSE EVENT IS EXPECTED IN THE CASE DATASET — 324

INDICATE ON A GRAPHICAL USER INTERFACE (GUI) THE ADVERSE EVENT IS UNEXPECTED IN THE CASE DATASET — 328

DETERMINE A SUBMISSION TIMEFRAME BASED ON THE REFERENCE SOURCE DOCUMENT AND THE EXPECTEDNESS OF THE ADVERSE EVENT — 332

OUTPUT THE CASE DATASET — 336

FIG. 3

SYSTEMS AND METHODS FOR ELECTRONICALLY MONITORING EXPECTED ADVERSE REACTIONS OF PHARMACEUTICAL PRODUCTS

CROSS-REFERENCE TO RELATED APPLICATIONS

This application is a continuation of U.S. patent application Ser. No. 17/691,751, filed Mar. 10, 2022, which claims priority to U.S. Provisional Patent Application No. 63/263,503, filed Nov. 3, 2021, which are both incorporated herein by reference.

TECHNICAL FIELD

The present disclosure relates to systems and methods for electronically monitoring expected adverse reactions of pharmaceutical products and determining expectedness in aggregate reports and cases.

BACKGROUND

Researchers, scientists, industry players, academics, government regulators, and other stakeholders are increasingly in need of efficient ways to monitor expected adverse reactions of pharmaceutical products and determine expectedness in aggregate reports and cases.

SUMMARY

One embodiment relates to a method for determining and indicating expectedness of an adverse event in an expectedness monitoring and analyzation system, the expectedness monitoring and analyzation system includes a provider computing system and a user computing device communicating with each other via a network. The provider computing system includes a document repository for storing electronic reference documents. The method includes receiving adverse event data associated with the adverse event and a clinical study. The method further includes determining an electronic reference document associated with the clinical study. The method further includes selecting the electronic reference document including a defined adverse reaction from the document repository. The defined adverse reaction includes an active start date. The method further includes generating a case dataset including at least a portion of the adverse event data. The method further includes determining the expectedness of the adverse event based on the defined adverse reaction of the electronic reference document and the adverse event data. The method further includes determining a submission timeframe associated with the case dataset based on the expectedness of the adverse event.

Another embodiment relates to a method for determining and indicating expectedness of a first adverse event and a second adverse event in an expectedness monitoring and analyzation system, the expectedness monitoring and analyzation system includes a provider computing system including a document repository for storing electronic reference documents. The method includes receiving adverse event data associated with the first adverse event, the second adverse event, and a medical product. The method further includes determining an electronic reference document associated with the medical product. The method further includes selecting the electronic reference document including a plurality of defined adverse reactions from the document repository. Each defined adverse reaction of the plurality of defined adverse reactions includes an active start date. The method further includes generating a first case dataset including at least a first portion of the adverse event data. The method further includes generating second case dataset including at least a second portion of the adverse event data. The method further includes determining the expectedness of the first adverse event based on a first adverse reaction of the plurality of defined adverse reactions and the adverse event data. The method further includes determining the expectedness of the second adverse event based on a second adverse reaction of the plurality of defined adverse reactions and the adverse event data. The method further includes determining a first submission timeframe associated with the first case dataset based on the expectedness of the first adverse event. The method further includes determining a second submission timeframe associated with the second case dataset based on the expectedness of the second adverse event.

This summary is illustrative only and is not intended to be in any way limiting. Other aspects, inventive features, and advantages of the devices or processes described herein will become apparent in the detailed description set forth herein, taken in conjunction with the accompanying figures, wherein like reference numerals refer to like elements.

BRIEF DESCRIPTION OF THE FIGURES

FIG. 2 is a flow diagram of a method for electronically monitoring expected adverse reactions of pharmaceutical products and automatically determining expectedness in an aggregate report, according to an example embodiment.

FIG. 3 is a flow diagram of a method for electronically monitoring expected adverse reactions of pharmaceutical products and automatically determining expectedness in a case, according to an example embodiment.

DETAILED DESCRIPTION

Figure 1:
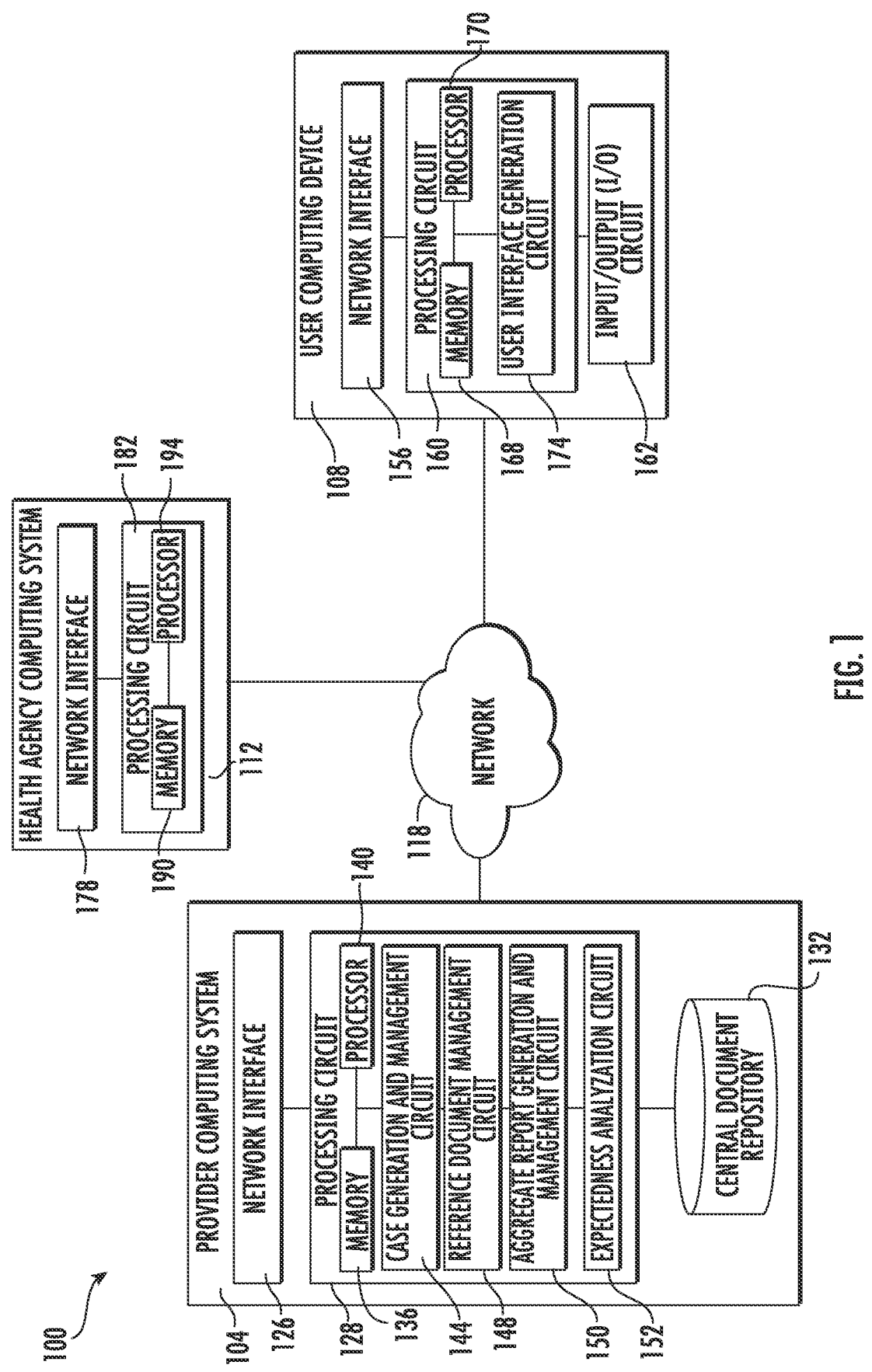
FIG. 1 is a component diagram of an adverse reaction expectedness monitoring and analyzation system, according to an example embodiment.

Referring generally to the figures, systems and methods for electronically monitoring expected adverse reactions and automatically determining expectedness in an aggregate report are disclosed. The systems and methods described herein provide for improved adverse event expectedness detection, and thereby help and improve the pharmacovigilance industry by more accurately tracking, capturing, and reporting expected or unexpected adverse events or reactions. For example, by automatically determining if received adverse event data associated with an adverse event is expected or unexpected based on an aggregate report type and the defined adverse reactions of a reference document, the present systems determine expectedness of cases and adverse events in real-time and allow for faster detection and submission of any serious adverse reactions (SARs) or serious unexpected suspected adverse reactions (SUSARs). Additionally, because the systems and methods described herein do not have to review each version of a reference document for potential cut-off dates and changes to expected adverse reactions, the systems and methods can automatically determine expectedness based on the aggregate report type and defined adverse reactions of the reference document (including the active start date and optional end date), which results in faster and less cumbersome expectedness monitoring and tracking and more focus on the reporting of the unexpected adverse events.

Moreover, because the systems and methods described herein automatically generate submissions to health authorities for adverse events and case datasets (cases), the present systems and methods reduce the overall time required for adverse events and case datasets to be reported to the correct health authorities, thereby helping the pharmaceutical industry overall. For instance, the systems and methods described herein automatically determine expectedness for each adverse event and case dataset and then determine a submission timeframe based on the expectedness of the adverse event and the seriousness of the adverse event. Next, the systems and methods described herein may generate a submission for each country or region in which the associated medical product is registered and automatically submit the submission including the case dataset and/or the adverse event data within the submission timeframe. As a result, the systems and methods described herein significantly speed up the reporting of adverse events and reactions including SARs and SUSARs, thereby providing the adverse event to the relevant health authorities quicker than in typical systems and giving the health authorities more time to report the adverse events to the public, which provides an improvement as compared to typical adverse event reporting methods and systems.

Additionally, the systems and methods described herein provide a technical solution to the technical problem of electronically monitoring and tracking expected and unexpected (defined) adverse reactions. For example, by electronically monitoring defined adverse reactions in a reference source information document (RSI) or other reference documents, the systems and methods described herein do not require repeated versioning of the reference document and use less processing power and memory, in comparison to typical adverse reaction monitoring systems. For instance, the systems and methods described herein may represent each defined adverse reaction within a reference document with a MedDRA code or term, an active start date, and an optional end date, as compared to versioning the entire RSI to indicate each change to adverse reaction expectedness. By doing so, the systems and methods described herein only store a single copy of the reference document for each medical product or study with changes being made to the expected adverse events of the reference, which saves on memory by not having to save multiple versions or copies of the reference document and processing power by not having to repeatedly replicate the reference document, in comparison to typical adverse reaction monitoring systems.

The systems and methods described herein further provide a technical solution to the technical problem of improving adverse event expectedness detection. For example, by automatically determining if received adverse event data associated with an adverse event is expected or unexpected based on an aggregate report type and the defined adverse reactions of the reference document, the present systems use less processing power. For instance, because the systems and methods described herein do not have to review each version of the reference document and instead can automatically determine expectedness based on the aggregate report type and the defined adverse reactions of the reference document (including the active start date and optional end date), the systems and methods perform less comparing and electronic file retrieval and therefore use less processing power.

In an illustrative scenario, a provider computing system may receive adverse event data associated with one or more adverse event of an associated medical product as well as a request to generate a section of an aggregate report. The request may include an aggregate report type, the associated medical product, a reporting period start date, and a reporting period end date. In some embodiments, the provider computing system receives a first request including the aggregate report type and the associated medical product, and a second request including the reporting period start date and the reporting period end date. Then, once the request is received, the provider computing system may determine and retrieve/select or receive a reference document based on the aggregate report type and the associated medical product from a central document repository. The reference document may include one or more defined adverse reactions each including an active start date (also referred to herein as active date start) and an optional end date (also referred to herein as an optional active date end). Next, the provider computing system may determine an expectedness cut-off date based on the aggregate report type, the reporting period start date, and/or the reporting period end date. Once the expectedness cut-off date is determined, the provider computing system may generate the section of the aggregate report including the one or more adverse events (e.g., in a listing, a chart, a table, etc.). Next, the provider computing system may determine expectedness for each of the one or more adverse events and indicate, within the section of the aggregate report, whether each adverse event was expected or unexpected. In some embodiments, the provider computing system may indicate on a graphical user interface (GUI) whether each adverse event was expected or unexpected. Further, the provider computing system may provide the section of the aggregate report to a user computing device or a health agency computing system (e.g., the FDA electronic submissions gateway).

As used herein, the term "event," "medical event," or "adverse event" can include any untoward medical occurrence which happens to either a patient or a subject in a clinical investigation/study or during regular use of a medical product that has been given to that person. For example, the "event," "medical event," or "adverse event" may encompass any signs which are unfavorable and unexpected for the patient or subject, including any abnormal laboratory findings such as a high blood pressure, a rapid heart rate, etc. The "event," "medical event," or "adverse event" can include symptoms, or a disease temporally associated with the use of a medical product and does not have to have been previously associated with that product. The term "event," "medical event," or "adverse event" can further include adverse reactions and serious adverse events such as death, life-threatening adverse experiences, inpatient hospitalization, congenital birth defects, disabilities, etc. Further, each "event," "medical event," or "adverse event" may be defined by the Medical Dictionary for Regulatory Activities (MedDRA) and associated with a specific MedDRA code. Moreover, "event information" "medical event information"

"adverse event information" "event data" "medical event data" or "adverse event data" can include information associated with the event such as the date of onset of the event, the date of cessation of the event, the type of event, the dictionary term, the dictionary code (e.g., MedDRA code), event comments, the outcome of the event, the location of the event (e.g., country where the event occurred), the event duration, patient data for a patient who endured or to which the event occurred, medical products that the patient consumed and/or dosages for the consumed medical products, the event rank, event contacts, the event type, and any associated event documents.

As used herein the term "adverse reaction" can include an adverse event for which there is a reasonable possibility or degree of certainty a specific medical product caused the adverse event. The degree of certainty or reasonable possibility may be determined by a medical professional or health care professional.

Additionally, as used herein the terms "information" and "data" may be used interchangeably such that one may be substituted for the other and vice versa.

As used herein, the term "case" or "case dataset" can include an Individual Case Safety Report (ICSR) as defined by the standard ISO/HL7 27953 of the International Standards Organization (ISO) as well as any past or future standards governing ICSRs of the ISO, the Food and Drug Administration (FDA), the European Medicines agency (EMA), or other national health agencies governing ICSRs. Moreover, "case information" "case data" or "case dataset" can include information associated with or included in the case such as adverse event data, case contact data, case priority data, case seriousness data, case documents, medical product registrations, patient data, and other data associated with a case as defined by the standard ISO/HL7 27953 as well as any past or future standards governing ICSRs of the ISO, the Food and Drug Administration (FDA), the European Medicines agency (EMA), or other national health agencies governing ICSRs.

As used herein, the term "periodic report" or "aggregate report" can include any report that is periodically (e.g., annually, semiannually) generated and provided to a health agency (e.g., the FDA, the EMA, etc.) for pharmacovigilance safety concerns and to report adverse events or adverse reactions associated with a specific medical product or a specific clinical trial. For example, the term "periodic report" or "aggregate report" can include a Drug Safety Update Report (DSUR), a Periodic Safety Update Report (PSUR), a Periodic Benefit-Risk Evaluation Report (PBRER), Periodic Adverse Drug Experience Report (PADER), or other periodic pharmacovigilance safety reports.

Referring now to FIG. 1, a system 100 for electronically monitoring expected adverse reactions and automatically determining expectedness is shown, according to an example embodiment. The system 100 includes a provider computing system 104, a user computing device 108, and a health agency computing system 112 connected by a secure network (e.g., a network 118).

The network 118 communicably and operably couples the provider computing system 104, the user computing device 108, and the health agency computing system 112 such that communicable and operable computing may be provided between the provider computing system 104, the user computing device 108, and/or the health agency computing system 112 over the network 118. In various embodiments, the network 118 includes any combination of a local area network (LAN), an intranet, the Internet, or any other suitable communications network, directly or through another interface.

The provider computing system 104 may be operated and managed by a provider (e.g., a software as a service (SaaS) provider, a cloud services provider, a software provider, a service provider, etc.) and may include a computer system (e.g., one or more servers (e.g., a cloud computing server) each with one or more processing circuits). In some embodiments, the provider computing system 104 may act as a host and provide an application (e.g., a web-based application, a mobile application, etc.) to the user computing device 108 over the network 118 in response to authenticating the respective computing device. As shown, the provider computing system 104 may include a network interface 126, a processing circuit 128, and a central document repository 132. In some embodiments, the provider computing system 104 may include an input/output circuit (e.g., similar to or the same as an input/output circuit 162 that will be described further herein).

The network interface 126 is structured to establish connections with the user computing device 108 and the health agency computing system 112 by way of the network 118. The network interface 126 includes program logic and/or hardware-based components that connect the provider computing system 104 to the network 118. For example, the network interface 126 may include any combination of a wireless network transceiver (e.g., a cellular modem, a broadband modem, a Bluetooth transceiver, a Wi-Fi transceiver, a Li-Fi transceiver, etc.) and/or a wired network transceiver (e.g., an Ethernet transceiver). In some embodiments, the network interface 126 includes the hardware and machine-readable media structured to support communication over multiple channels of data communication (e.g., wireless, Bluetooth, near-field communication (NFC). In some embodiments, the network interface 126 includes cryptography logic and capabilities to establish a secure communications session.

Additionally, the network interface 126 may include AS2 gateway logic that includes programmable instructions that facilitate communication (transmission and receipt) using the AS2 Gateway communication protocol (as specified in Request for Comment (RFC) 4130) over the network 118 via the network interface 126. For example, using the AS2 gateway logic, the network interface 126 may transmit or receive files (e.g., a source file including adverse event data, a case, a case dataset, etc.) or other data to the health agency computing system 112 and/or the user computing device 108 using the AS2 Gateway protocol.

The processing circuit 128, as shown, comprises a memory 136, a processor 140, a case generation and management circuit 144, a reference document management circuit 148, an aggregate report generation and management circuit 150, and an expectedness analyzation circuit 152. The memory 136 includes one or more memory devices (e.g., RAM, NVRAM, ROM, flash memory, hard disk storage, etc.) that store data and/or computer code for facilitating the various processes described herein. That is, in operation and use, the memory 136 stores at least portions of instructions and data for execution by the processor 140 to control the processing circuit 128. The memory 136 may be or include tangible, non-transient volatile memory and/or non-volatile memory. The processor 140 may be implemented as a general-purpose processor, an application specific integrated circuit (ASIC), one or more field programmable gate array (FPGAs), a digital signal processor (DSP), a group of processing components or other suitable electronic processing components.

As described herein, the case generation and management circuit 144 is structured or configured to receive adverse event data associated with one or more specific medical products or clinical trials/studies (which may be associated or testing one or more specific medical products) and generate a case including case data, in response. For example, the case generation and management circuit 144 may receive an email or an E2B XML file including adverse event data associated with a specific medical product (e.g., drug X) or a specific clinical trial (e.g., clinical trial Y) testing a specific medical product. In response, the case generation and management circuit 144 may generate or determine case data based on the adverse event data and a case including the case data. In some embodiments, the adverse event data may be determined (e.g., by the user of the user computing device 108 or by a health care professional (HCP) of an HCP computing device (not shown)) as being associated with an adverse reaction or a serious adverse reaction (SAR) of the medical product or the clinical trial/study. The case generation and management circuit 144 may store the case and the associated case data within the central document repository 132 and/or electronically provide or transmit the case to the health agency computing system 112 (e.g., the FDA electronic submissions gateway). In some embodiments, the adverse event data and/or the case data determined from the adverse event data may include a date/time of receipt or a date/time at which the associated adverse event or reaction occurred.

Additionally, the case generation and management circuit 144 may be configured or structured to generate a submission timeframe based on the expectedness or listedness of the adverse event. For example, the case generation and management circuit 144 may determine the case dataset is to be submitted within 15 days (e.g., to the FDA) based on the adverse event being unexpected. In another example, the case generation and management circuit 144 may determine the case dataset is to be submitted by the end of the month (e.g., to the FDA) based on the adverse event being an expected serious adverse event. In some embodiments, the case generation and management circuit 144 may further generate an alert, a submission identifier, or an electronic submission indicating the date on which the case is to be submitted by. In some embodiments, the case generation and management circuit 144 may automatically electronically submit the case dataset to the respective health agency (e.g., via the network interface 126) by the submission deadline or within the submission timeframe. In some embodiments, the case generation and management circuit 144 may generate the submission timeframe based on the reference document.

The reference documents management circuit 148 is configured or structured to intake or generate and manage one or more RSIs or other reference documents (e.g., an investigational brochure (IB), a company core safety information document (CCSI) (also referred to as a company core datasheet), and/or a region-specific labelling document (e.g., a summary of product characteristics (SmPC) in Europe, a United States Prescribing information document (USPI), etc.)). Reference documents are documents that identify or list all adverse events observed associated with a medical product during use of a medical product (e.g., in a clinical trial or marketing of the medical product) and typically defines which adverse events or adverse reactions are expected for the medical product being administered to patients or subject in a clinical trial. Typically, the reference document is updated once updated annually. In some embodiments, the reference document is updated more or less than annually (e.g., semi-annually, quarterly, monthly, daily, every two years, etc.). Further, each reference document may be associated with or directed toward a specific medical product (e.g., drug X) or a specific clinical study and define or include defined (i.e., expected or unexpected) adverse reactions or events that a patient may experience during use of the specific medical product. The defined adverse reactions may be adverse reactions that are defined by a user (e.g., the user of the user computing device 108) as being expected or unexpected when taking a specific medical product and between one or more dates. In this regard, each defined adverse reaction may include an expectedness field indicating whether the defined adverse reaction is expected or unexpected, a MedDRA code or term representing the adverse reaction, a medical product associated with the adverse reaction, and two or more dates/times in which the defined adverse reaction is in effect. In this regard, the reference documents management circuit 148 may be configured to receive an indication or request to update each specific reference document and may add or remove defined adverse reactions, in response.

The aggregate report generation and management circuit 150 is structured or configured to receive a request to generate one or more sections of an aggregate report of adverse events associated with a medical product (e.g., an electronic aggregate report) including or identifying an aggregate report type (e.g., a Drug Safety Update Report (DSUR), a Periodic Safety Update Report (PSUR), a Periodic Benefit-Risk Evaluation Report (PBRER), etc.), a reporting period start date, and/or a reporting period end date. In some embodiments, the request only includes or identifies a reporting period start date and the reporting period end date is determined based on the aggregate report type as each aggregate report type has a specific reporting period. In response to receiving the request to generate the aggregate report, the aggregate report generation and management circuit 150 may generate the aggregate report. In some embodiments, the request further includes or identifies a reference document associated with the medical product and from which expectedness is determined. In other embodiments, the reference document is determined based on the medical product and the type of the aggregate report. For example, the aggregate report generation and management circuit 150 may determine the reference document for a DSUR is the IB associated with the specific medical product (as defined in the E2F DSUR Guidance).

In some embodiments, the aggregate report generation and management circuit 150 only generates one or more ds of the aggregate report (e.g., a cumulative tabulation of serious adverse events or SARS, a list of subject/patients who died during the reporting period, a table including a line listing of serious adverse events or SARS, etc.) and the user of the user computing device 108 manually generates and/or provides other sections of the aggregate report (e.g., the executive summary, the introduction, etc.) to the provider computing system 104. In some embodiments, the request to generate the aggregate report may include or indicate the sections of the aggregate report the aggregate report generation and management circuit 150 is to generate.

Once the aggregate report generation and management circuit 150 has generated the aggregate report (e.g., generated one or more sections of the aggregate report and/or received the other sections) as well as identified or indicated one or more adverse reactions that are expected (as will be described further herein), the aggregate report generation and management circuit 150 may interface with the network interface 126 to provide or transmit the electronic aggregate report to the user computing device 108 or a third-party computing device (not shown). In other embodiments, the aggregate report generation and management circuit 150 may interface with the network interface 126 to provide or transmit the sections of the electronic aggregate report to the user computing device 108 or the third-party computing device.

The expectedness (and/or listedness) analysis circuit 152 may be configured or structured to receive the reference document associated with the medical product (e.g., from the central document repository 132) as well as cases and/or adverse event data associated with adverse events or adverse reactions that occurred within the reporting period and determine the expectedness of each adverse reaction or case. For example, the expectedness analysis circuit 152 may determine an expectedness cut-off date based on the aggregate report type, the reporting period start date, and the reporting period end date. The expectedness cut-off date is the date for which the provider computing system 104 is to determine whether the reference document included the adverse reaction or adverse event as expected, also referred to herein as "listed" or "labelled." In some embodiments, "expected" "unexpected" or "expectedness" may refer to or applied to an adverse event of a drug or medical product that is currently under investigation or development (e.g., in a clinical study or pre-marketed). In comparison, "listed" "labelled" "unlisted" or "listedness" may refer to or be applied to an adverse event of a drug or medical product that is marketed. Moreover, as described herein, each aggregate report type may have different rules on when the expectedness cut-off date is to be. For example, if the aggregate report is a DSUR aggregate report, the E2F DSUR Guidance indicates the expectedness cut-off date is to be the start of the reporting period (i.e., the reporting period start date). In comparison, the PSUR aggregate report can use the start of the reporting period or the end of the reporting period, based on how long the medical product has been on the market. In this regard, the expectedness analysis circuit 152 may receive the adverse event data associated with each adverse event that occurred after the start of the reporting period (e.g., a MedDRA term or code) and determine whether that adverse event is expected or listed on the reference document (e.g., by determining whether the reference document includes the MedDRA term or code) based on the cut-off date and the reference document itself.

Additionally, the expectedness analysis circuit 152 may be configured or structured to determine one or more seriousness exclusions associated with the adverse event, the medical product, or the study. The seriousness exclusions may include one or more seriousness criteria of the specific case and adverse event (e.g., the adverse event resulted in death, the adverse event resulted in prolonged hospitalization, and the like) which override the expectedness of the adverse reaction. For example, the expectedness analysis circuit 152 may receive a reference document associated with the specific medical product which includes the adverse reaction "fever" as expected. However, the expectedness analysis circuit 152 may further receive a seriousness exclusion which identifies any adverse event with a seriousness that results in death as being unexpected. In this regard, the expectedness analysis circuit 152 may determine the adverse event "fever" includes a seriousness of results in death and determine the adverse event is unexpected.

In some embodiments, the expectedness analysis circuit 152 may be configured or structured to automatically determine an undefined adverse reaction or event (e.g., an adverse event or reaction that is not identified or defined as expected or unexpected in the reference document) is expected. In other embodiments, the expectedness analysis circuit 152 may be configured or structured to automatically determine an undefined adverse event is unexpected. In some embodiments, the expectedness analysis may require manual determination of expectedness for undefined adverse events. In other embodiments, the reference document may specify the action the expectedness analysis circuit 152 is to take if the adverse event is undefined.

Once the expectedness analysis circuit 152 has determined whether each adverse event is expected or not, the expectedness analysis circuit 152 may indicate on the electronic aggregate report whether each adverse event is expected or unexpected. In some embodiments, the expectedness analysis circuit 152 may do so by highlighting or marking each unexpected adverse event on the aggregate report (e.g., with an asterisk and a footnote, with a highlight and a footnote, with a symbol and a footnote, etc.). In this regard, expected adverse events may be indicated as such by not including a marking and unexpected adverse reaction may be indicated as such by including a marking. In other embodiments, the expectedness analysis circuit 152 may indicate each expected or unexpected adverse event in other ways (e.g., a listing of all expected adverse reactions and a listing of all unexpected adverse reactions, etc.).

The central document repository 132 is a repository (e.g., a database) that is structured or configured to receive, store, and manage documents (e.g., electronic documents, electronic reference documents, etc.), files, and/or data object associated with the documents or files. For example, the central document repository 132 may receive newly generated reference documents, cases, and/or aggregate reports and store each therein. In another example, the central document repository 132 may receive the case data and/or the adverse event data and an associated data object (e.g., a case data object). For each document or data object stored within the central document repository 132, the central document repository 132 may further generate or determine version data associated with each to capture and save any changes made to the document or data object. In some embodiments, reference documents (e.g., a CCSI) stored within the central document repository 132 may not include version data and, instead, may include defined adverse reactions with an active start date and an optional active end date, as will be described further herein. In some embodiments, each document and/or associated data object may include medical product data identifying a specific medical product or clinical study the document is associated with. To do so, the central document repository 132 can be structured according to various database types, such as, relational, hierarchical, network, flat, point-in time, and/or object relational. In some embodiments, the central document repository 132 includes a plurality of nonvolatile/non-transitory storage media such as solid-state storage media, hard disk storage media, virtual storage media, cloud-based storage drives, storage servers, and/or the like.

Still referring to FIG. 1, the user computing device 108 can be any type of computing device or computing system. For instance, the user computing device 108 can be one or more of a mobile phone, a tablet computer, a laptop computer, a smart watch, a server computer system, or any other internet-connected device. In operation, the user computing device 108 may communicate and interface with the provider computing system 104 via the network 118 to generate and provide a request to generate an aggregate report to the provider computing system 104. For example, the user of the user computing device 108 may interface with the provider computing system 104 to decide or set the aggregate report type, the associated medical product of the aggregate report, the reporting period start date, and/or the reporting period end date. Once each field is set, the user of the user computing device 108 may further interface with the provider computing system 104 to generate and provide the request to the provider computing system 104. Further, in some embodiments, the user computing device 108 may provide adverse event data to the provider computing system 104 (e.g., in an E2B XML file, in an email, etc.) for generating a case and inclusion in an aggregate report. As shown, the user computing device 108 may include a network interface 156, a processing circuit 160, and the input/output (I/O) circuit 162.

The network interface 156 is structured to establish connections with the provider computing system 104 and/or the health agency computing system 112 by way of the network 118. The network interface 156 includes program logic and/or hardware-based components that connect the user computing device 108 to the network 118. For example, the network interface 156 may include any combination of a wireless network transceiver (e.g., a cellular modem, a broadband modem, a Bluetooth transceiver, a Wi-Fi transceiver, a Li-Fi transceiver, etc.) and/or a wired network transceiver (e.g., an Ethernet transceiver). In some embodiments, the network interface 156 includes the hardware and machine-readable media structured to support communication over multiple channels of data communication (e.g., wireless, Bluetooth, near-field communication (NFC). In some embodiments, the network interface 156 includes cryptography logic and capabilities to establish a secure communications session.

The processing circuit 160, as shown, comprises a memory 168, a processor 170, and a user interface generation circuit 174. The memory 168 includes one or more memory devices (e.g., RAM, NVRAM, ROM, flash memory, hard disk storage, etc.) that store data and/or computer code for facilitating the various processes described herein. That is, in operation and use, the memory 168 stores at least portions of instructions and data for execution by the processor 170 to control the processing circuit 160. The memory 168 may be or include tangible, non-transient volatile memory and/or non-volatile memory. The processor 170 may be implemented as a general-purpose processor, an application specific integrated circuit (ASIC), one or more field programmable gate array (FPGAs), a digital signal processor (DSP), a group of processing components or other suitable electronic processing components.

The user interface generation circuit 174 may be configured to receive a user interface (e.g., a web interface in an HTML file and related files, a downloaded graphical user interface, etc.) from the provider computing system 104 and render or generate the user interface on the user computing device 108 via the I/O circuit 162. In this way, the provider computing system 104 may generate one or more user interfaces and provide the one or more user interfaces to the user interface generation circuit 174 to be rendered on the user computing device 108 (e.g., on a display of the I/O circuit 162 of the user computing device 108).

The I/O circuit 162 is structured to receive communications from and provide communications to the user of the user computing device 108 (e.g., the user). In this regard, the I/O circuit 162 is structured to exchange data with the processing circuit 160 to provide output to the user and to receive input from the user. As a result, the I/O circuit 162 may include a display that may be manipulated by the application. In some embodiments, the I/O circuit 162 may also include a keyboard, a mouse, a joystick, a touch screen, touch areas, soft keys, a microphone, a speaker, a vibration mechanism, a sensor, a RFID scanner, or other input/output devices described herein.

Still referring to FIG. 1, the health agency computing system 112 can be any type of computing device or computing system and is associated or managed by a health agency (e.g., the FDA, the EHA, Health Canada, etc.). For instance, the health agency computing system 112 may be the Electronics Submission Gateway (ESG) of the FDA through which one or more E2B XML files (e.g., case datasets) may be received from or provided to. In operation, the health agency computing system 112 may communicate with the provider computing system 104 or the user computing device 108 to send and/or receive one or more case datasets associated with adverse events (e.g., E2B files, PDF files, FDA 3500A PDF files, etc.). Further, the health agency computing system 112 112 is shown to include a network interface 178 and a processing circuit 182

The network interface 178 is structured to establish connections with the provider computing system 104 and/or the user computing device 108 by way of the network 118. The network interface 178 includes program logic (e.g., AS2 Gateway logic) and/or hardware-based components that connect the health agency computing system 112 to the network 118. For example, the network interface 178 may include any combination of a wireless network transceiver (e.g., a cellular modem, a broadband modem, a Bluetooth transceiver, a Wi-Fi transceiver, a Li-Fi transceiver, etc.) and/or a wired network transceiver (e.g., an Ethernet transceiver). In some embodiments, the network interface 178 includes the hardware and machine-readable media structured to support communication over multiple channels of data communication (e.g., wireless, Bluetooth, near-field communication (NFC). In some embodiments, the network interface 178 includes cryptography logic and capabilities to establish a secure communications session.

The processing circuit 182, as shown, comprises a memory 190 and a processor 194. The memory 190 includes one or more memory devices (e.g., RAM, NVRAM, ROM, flash memory, hard disk storage, etc.) that store data and/or computer code for facilitating the various processes described herein. That is, in operation and use, the memory 190 stores at least portions of instructions and data for execution by the processor 194 to control the processing circuit 182. The memory 190 may be or include tangible, non-transient volatile memory and/or non-volatile memory. The processor 194 may be implemented as a general-purpose processor, an application specific integrated circuit (ASIC), one or more field programmable gate array (FPGAs), a digital signal processor (DSP), a group of processing components or other suitable electronic processing components.

Referring now to FIG. 2, a method 200 of electronically monitoring expected adverse reactions of pharmaceutical products and automatically determining expectedness or listedness in an aggregate report is shown, according to an example embodiment. Method 200 can be carried out by the system of FIG. 1. More particularly, the method 200 can be carried out by the processing circuit 128 of the provider computing system 104 and through communication with the user computing device 108 and/or the health agency computing system 112.

Method 200 commences at step 204 at which the provider computing system 104 receives adverse event data associated with one or more adverse events of a specific associated medical product or a specific clinical trial. In some embodiments, the adverse event data may be received as associated with an adverse event and forwarded or provided to a medical reviewer (e.g., at a medical reviewer computing device) who determines the adverse event is an adverse reaction associated with the specific medical product (by determining causality). In this regard, at or after step 204, the provider computing system may use the adverse event data to generate a case, including case data, associated with the specific medical product and receive an indication the adverse event data is associated with an adverse reaction. The adverse event data or case data may include data pertaining to the adverse event such as the date of onset of the event, the date of cessation of the event, the type of event, the event code (e.g., MedDRA code), seriousness data indicating the seriousness of the event, event comments, the outcome of the event, the location of the event (e.g., country where the event occurred), the event duration, patient data for a patient who endured or to which the event occurred, medical products that the patient consumed and/or dosages for the consumed medical products, the event rank, event contacts, the event type, and/or any associated event documents. In some embodiments, the adverse event data may be received from the user computing device 108 or the health agency computing system 112 (e.g., the FDA electronic submissions gateway) in a source document (e.g., an E2B XML file, an email and email attachments, a PDF document, etc.). In some embodiments, the adverse event data is associated with one or more clinical studies or trials, and each clinical study or trial is associated with one or more medical products (e.g., a drug being studied in the clinical study). In other embodiments, the adverse event data is associated with one or more marketed medical products.

Once the provider computing system 104 has received the adverse event data, the method 200 proceeds to step 206 at which the provider computing system 104 receives a request to generate an aggregate report (e.g., an electronic aggregate report) or a section of the aggregate report. The request may include or identify the aggregate report type, the associated medical product, the reporting period start date, and the reporting period end date. In some embodiments, the request may further identify or include an associated customer or organization, one or more case filters and/or a case listing of cases to be used in generating the aggregate report, a listing of sections of the aggregate report to generate, and/or an expectedness cut-off date to use (as shown in FIG. 3 and will be discussed further herein). In some embodiments, the request identifies an associated clinical trial or study, which is associated with a specific medical product. In this regard, the provider computing system 104 may determine one or more associated medical products based on the associated clinical trial or study of the request.

In some embodiments, at step 204, the provider computing system 104 may receive multiple pieces of adverse event data each associated with one or more adverse events. For example, over the course of 6 months or a year (i.e., a typical reporting period), the provider computing system 104 may receive multiple pieces of adverse event data, generate a case for each piece of adverse event data including a date/time of the adverse event (e.g., a date/time of onset), and store each case within the central document repository 132. Then, after receiving the request to generate the section of the aggregate report (i.e., after step 206), the provider computing system 104 may retrieve or receive each case associated with the specific medical product that occurred within the reporting period (e.g., between the reporting period start date and the reporting period end date) from the central document repository 132. In some embodiments, the provider computing system 104 may only retrieve or receive cases from the central document repository 132 that meet or match the case filters and/or the case listing of the request.

Once the provider computing system 104 has received the request to generate the section of the aggregate report, the method 200 proceeds to step 208 at which the provider computing system 104 determines a reference document (e.g., an electronic reference document) based on the aggregate report type and the associated medical product. As described herein, each different aggregate report (e.g., a DSUR, a PSUR, a PBRER, etc.) may use a different reference document (e.g., a CCSI, an IB, a region-specific labelling document) to determine expectedness of each adverse event. In this regard, the provider computing system 104 may determine the specific type of reference document to use and the reference document associated with the specific medical product that is to be used. For example, the provider computing system 104 may determine because the aggregate report to be generated is a DSUR for drug X, the correct reference document is the IB for drug X. Further, the provider computing system 104 may then search or query the central document repository 132 for the corresponding reference document (e.g., the IB for drug x) to determine the specific reference document to be used in determining expectedness.

Once the provider computing system 104 has determined the reference document to be used in determining expectedness, the method 200 may proceed to step 212 at which the provider computing system 104 retrieves or receives the electronic reference document from the central document repository 132. In some embodiments, the reference document may be retrieved or received by the provider computing system 104 from another computing device or computing system (e.g., the user computing device 108 or a health agency computing system 112 (e.g., the FDA electronic submissions gateway)), in response to determining that the central document repository 132 does not include or store the reference document. Moreover, the reference document may include or identify one or more defined adverse reactions or events that each include an active start date and an optional active end date as well as an expectedness field indicating whether the defined adverse reaction indicates the adverse event is expected or unexpected. In this regard, the central document repository 132 may not store each reference document with version data but instead, each reference document or associated data object may include multiple defined (i.e., expected or unexpected) adverse reactions that include an active start date and an optional active end date.

In some embodiments, the electronic reference document may include or identify one or more seriousness exclusions that include one or more seriousness types (e.g., results in death, results in prolonged hospitalization, etc.). In some embodiments, the seriousness exclusions may be specific to one or more adverse reactions and be included in the adverse reactions. In other embodiments, the seriousness exclusions may apply to all adverse reactions of the reference document. Further, the reference document may include or identify an undefined adverse event action. The undefined adverse event action may specify the action the provider computing system 104 is to take while determining the expectedness or listedness of an undefined adverse event. For example, the undefined adverse event action may indicate all undefined adverse events are to be identified as expected, as unexpected, as requiring manual expectedness determination, and the like.

Once the provider computing system 104 has received the reference document the method 200 proceeds to step 216 at which the provider computing system 104 determines an expectedness cut-off date. The expectedness cut-off date may be determined based on the aggregate report type, the reporting period start date, and the reporting period end date. For example, the provider computing system 104 may determine the expectedness cut-off date for a DSUR aggregate report is the reporting period start date (as defined in the E2F DSUR Guidance). In another example, the provider computing system 104 may determine the expectedness cut-off date for a PBRER aggregate report is the reporting period end date. Additionally, for aggregate reports which can have multiple expectedness cut-off dates (e.g., the PSUR aggregate report), the provider computing system may determine each expectedness cut-off date and provide each to the user computing device 108 for selection by the user (e.g., as a part of the request, see FIG. 3). In this regard, the expectedness cut-off date may be determined based on the aggregate report type, the reporting period start date, the reporting period end date, and/or the expectedness cut-off date indication selected by the user and received in the request. Accordingly, in some embodiments, step 216 and determining the expectedness cut-off date may take place prior to or between steps 206, 208, and/or 212. Further, in some embodiments, the provider computing system 104 may receive a first request to generate an aggregate report including an aggregate report type at step 206. Then, after receiving the first request, the provider computing system 104 determines the expectedness cut-off date in terms of being one or more of the beginning (or first day) of the reporting period or the end (or the last day) of the reporting period, without having received the specific reporting period start date and reporting period end date, and provide these expectedness cut-off options to the user for selection (see discussion regarding FIG. 3). After providing the expectedness cut-off option(s) to the user computing device 108, the provider computing system 104 may receive a second request including the associated medical product, a reporting period start date, and a reporting period end date and proceed with steps 208-216.

Once the provider computing system 104 has determined the expectedness cut-off date, the method 200 proceeds to step 220 at which the provider computing system 104 generates the section of the aggregate report based on the aggregate report type and the adverse event data. For example, the provider computing system 104 may generate sections of the aggregate report in which the adverse events are listed or indicated (e.g., a cumulative tabulation of serious adverse events or SARS, a list of subject/patients who died during the reporting period, a table including a line listing of serious adverse events or SARS, etc.). In this regard, the provider computing system 104 may generate the aggregate report (or portions/sections thereof) to include the one or more adverse events (i.e., at least a portion of the adverse event data identifying the adverse events). In some embodiments, the provider computing system 104 may generate the sections of the aggregate report identified by the listing of the sections of the aggregate report to generate in the request. In some embodiments, at step 220, the provider computing system 104 may generate the aggregate report by generating one or more sections of the aggregate report and receiving other sections of the aggregate report.

In some embodiments, prior to step 220, the provider computing system 104 may retrieve or receive cases associated with the specific medical product that occurred within the reporting period (e.g., between the reporting period start date and the reporting period end date) from the central document repository 132. Then, at step 220, the provider computing system 104 may generate the one or more sections of the aggregate report to include the case data or adverse event data of each case based on the cases and the aggregate report type.

Once the provider computing system 104 has generated one or more sections of the aggregate report, the method 200 proceeds to step 224 at which the provider computing system 104 determines if each adverse event of the one or more adverse events is expected or unexpected based on the one or more defined adverse reactions of the reference document. Steps 224-232 may be understood as being a part of the generating process of step 220 as changes are still occurring within one or more sections of the aggregate report. In this regard, it should be understood that step 224 may take place prior or directly prior to step 220 and steps 228-232 may be performed as a part of step 220. For example, the provider computing system 104 may determine whether each adverse event is expected or unexpected and then indicate whether each is expected or unexpected in the aggregate report while generating the aggregate report.

To determine whether the adverse event is expected or unexpected, the provider computing system 104 may first determine whether each adverse event is included as a defined adverse reaction within the respective reference document (e.g., by determining if the reference document includes or identifies the MedDRA term or code associated with the adverse reaction at all (e.g., included in the adverse event data)). If the adverse event is not listed as a defined adverse reaction, the provider computing system 104 may take the action of the undefined adverse event action (e.g., mark as expected, mark as unexpected, send a notification to the user computing device 108 requesting a manual selection, etc.). In comparison, if the adverse event is listed as a defined adverse reaction, the provider computing system 104 may compare the expectedness cut-off date to the active start date and/or the optional active end date of the defined adverse reaction. If the expectedness cut-off date is (inclusively) between the active start date and the optional active end date or is (inclusively) after the active start date (when there is no optional active end date), the provider computing system 104 may determine the adverse event is expected or unexpected (as indicated on the defined adverse reaction) and proceed to step 228 or 232. If the expectedness cut-off date is outside of the active start date and the optional end date or is before the active start date, the provider computing system 104 may take the action of the undefined adverse event action (e.g., mark as expected, mark as unexpected, send a notification to the user computing device 108 requesting a manual selection, etc.), and proceed to step 228 or 232. In some embodiments, if the adverse event is undefined, the provider computing system 104 may automatically determine the adverse event is expected. In other embodiments, if the adverse event is undefined, the provider computing system 104 may automatically determine the adverse event is unexpected. Inclusively between includes the active start date and the optional active end date, and inclusively after includes the active start date.

In some embodiments, the provider computing system 104 may determine whether each adverse event is expected or unexpected based on the one or more defined adverse reactions of the reference document, the seriousness exclusions of the reference document, the seriousness of each of the adverse events, and/or the undefined adverse event action of the reference document. For example, the reference document may include the adverse event "rash" as an expected adverse reaction, but also include a seriousness exclusion of "results in death." Accordingly, if the adverse event is a rash with a seriousness "results in death," the provider computing system 104 may determine the adverse event is unexpected. In another example, the reference document may include an undefined adverse event action of "mark as expected." Accordingly, if the adverse event is not defined by the adverse reactions of the reference document, the provider computing system 104 may determine the adverse event is expected. In some embodiments, if an adverse event corresponds to a seriousness exclusion (i.e., has a seriousness identified by the seriousness exclusion), the provider computing system 104 automatically sets the adverse event to unexpected.

If at step 224 the provider computing system 104 determine the adverse event is expected, the method 200 proceeds to step 228 at which the provider computing system 104 indicates the adverse event is expected in the one or more sections of the aggregate report. In some embodiments, at step 228, the provider computing system 104 further indicates on a graphical user interface (GUI), that is displayed on the user computing device 108, that the adverse event is expected in the section of the aggregate report by displaying the section of the aggregate report. As described herein, the provider computing system 104 may indicate an adverse event is expected in one or more ways such as by specifically emphasizing, marking, (e.g., with an asterisk and a footnote, with a number and a footnote, with another specific character and a footnote, etc.) or highlighting the expected adverse event in comparison to the unexpected adverse events. In another example, the provider computing system may indicate an adverse event is expected by providing a specific listing of all expected adverse events or reactions.

In comparison, if at step 224 the provider computing system 104 determines the adverse event is unexpected, the method 200 proceeds to step 232 at which the provider computing system 104 indicates the adverse event is unexpected in the one or more sections of the aggregate report. In some embodiments, at step 232, the provider computing system 104 further indicates on a graphical user interface (GUI), that is displayed on the user computing device 108, that the adverse event is expected in the section of the aggregate report by displaying the section of the aggregate report. As described herein, the provider computing system 104 may indicate an adverse event is unexpected in one or more ways such as by specifically emphasizing, marking, (e.g., with an asterisk and a footnote, with a number and a footnote, with another specific character and a footnote, etc.) or highlighting the unexpected adverse event in comparison to the expected adverse events. In another example, the provider computing system may indicate an adverse event is unexpected by providing a specific listing of all unexpected adverse reactions or events.

In some embodiments, the provider computing system 104 may only mark or identify unexpected adverse events in the one or more sections of the aggregate report such that step 228 is skipped. For example, by indicating each adverse event is unexpected (e.g., with a specific character and a footnote), a reader of the adverse report can also determine the expected adverse events (due to the lack of the indication).

In some embodiments, once the one or more sections of the aggregate report are generated (such that unexpected and/or expected adverse events are indicated in the one or more sections of the aggregate report), provider computing system 104 may provide the one or more sections of the aggregate report to the user computing device 108 or the health agency computing system 112 (e.g., the FDA gateway). In other embodiments, the provider computing system 104 may receive the remaining portions of the aggregate report, compile the aggregate report including the generated and received sections of the aggregate report, and provide the aggregate report to the user computing device 108 or the health agency computing system 112 (e.g., the FDA gateway). In one example, the aggregate report may be stored in the form of an electronic file (e.g., an XML file, a word document, an unmodifiable file (e.g., a PDF file), etc.) and provided to one or more of the user computing device 108 or the health agency computing system 112. In another example, the aggregate report may be first stored in the central document repository 132 and then provided or submitted to one or more of the user computing device 108 or the health agency computing system 112 as an electronic file.

Referring now to FIG. 3, a method 300 of electronically monitoring expected adverse reactions of pharmaceutical products and automatically determining expectedness or listedness of an adverse event is shown, according to an example embodiment. While different overall, it should be understood that any steps or discussion of the method 300 may be applied or included within the method 200, and vice versa. For example, the method 200 may include any of the steps 304-336, after or before any steps included in the method 200, and the method 300 may include any of the steps 204-232, after or before any of the steps included in the method 300. Method 300 can be carried out by the system of FIG. 1. More particularly, the method 300 can be carried out by the processing circuit 128 of the provider computing system 104 and through communication with the user computing device 108 and/or the health agency computing system 112.

Method 300 commences at step 304 at which the provider computing system 104 receives adverse event data associated with one or more adverse events of a specific associated medical product (e.g., a marketed medical product) or a specific clinical trial. In some embodiments, the adverse event data may be received as associated with an adverse event and forwarded or provided to a medical reviewer (e.g., at a medical reviewer computing device) who determines the adverse event is an adverse reaction associated with the specific medical product (by determining causality). The adverse event data may include data pertaining to the adverse event such as date data indicating the date of onset of the event, the time of onset of the event, the date of cessation of the event, seriousness data indicating the seriousness of the event, the type of event, the event code (e.g., MedDRA code), event comments, the outcome of the event, the location of the event (e.g., country where the event occurred), the event duration, patient data for a patient who endured or to which the event occurred, medical products that the patient consumed, dosages for the consumed medical products, the event rank, event contacts, the event type, and/or any associated event documents. In some embodiments, the adverse event data may be received from the user computing device 108 or the health agency computing system 112 (e.g., the FDA electronic submissions gateway) in a source document (e.g., an E2B XML file, an email and email attachments, a PDF document, etc.). In some embodiments, the adverse event data is associated with one or more clinical studies or trials, and each clinical study or trial is associated with one or more medical products. In other embodiments, the adverse event data is associated with one or more marketed medical products.

Once the provider computing system 104 has received the adverse event data, the method 300 proceeds to step 306 at which the provider computing system 104 receives a request to generate a case dataset for or associated with the adverse event. In some embodiments, in response to receiving the request, the provider computing system 104 may verify the adverse event data is complete and/or request or generate any additional case data (e.g., priority of the case, etc.). In some embodiments, in response to receiving the request, the provider computing system 104 may determine if the case dataset and/or the adverse event data is a duplicate and/or associated with any other cases (e.g., is a follow up case). If the case dataset and adverse event data is not a duplicate, the method 300 may proceed. If the case dataset is a follow up case, the provider computing system 104 may link the case dataset to the original case.

Once the provider computing system 104 has received the request to generate the case dataset, the method 300 proceeds to step 308 at which the provider computing system 104 determines a reference document (e.g., an electronic reference document) associated with the study or the medical product. In some embodiments, the provider computing system 104 may determine multiple electronic reference documents associated with the study or the medical product at step 308. For example, the provider computing system 104 may determine the specific medical product has an associated CCSI, an associated SmPC, and an associated USPI at step 308 by querying the central document repository 132 for all reference documents associated with the specific medical product or study.

Once the provider computing system 104 has determined the one or more electronic reference documents associated with the medical product or the study, the method 300 may proceed to step 312 at which the provider computing system 104 retrieves or receives each of the electronic reference documents from the central document repository 132. In some embodiments, one or more of the reference documents may be retrieved or received by the provider computing system 104 from another computing device or computing system (e.g., the user computing device 108 or the health agency computing system 112 (e.g., the FDA electronic submissions gateway)), in response to determining that the central document repository 132 does not include or store one or more of the reference documents. Moreover, the reference document may include or identify one or more expected adverse reactions or events that each include an active start date and an optional active end date. In this regard, the central document repository 132 may not store each reference document with version data but instead, each reference document or associated data object may include multiple expected or unexpected adverse reactions that include an active start date and an optional active end date.

In some embodiments, each of the electronic reference documents may include or identify one or more seriousness exclusions that include one or more seriousness types (e.g., results in death, results in prolonged hospitalization, etc.). In some embodiments, the seriousness exclusions may be specific to one or more adverse reactions and be included in the adverse reactions. In other embodiments, the seriousness exclusions may apply to all adverse reactions of the reference source document. Further, the reference document may include or identify an undefined adverse event action. The undefined adverse event action may specify the action the provider computing system 104 is to take while determining the expectedness or listedness of an undefined adverse event. For example, the undefined adverse event action may indicate all undefined adverse events are to be identified as expected, as unexpected, as requiring manual expectedness determination, and the like. In some embodiments, steps 308 and/or 312 (at which the provider computing system 104 determines and receives the electronic reference document(s)) may take place prior to step 306 (at which the provider computing system 104 receives a request to generate the case dataset).

Once the provider computing system 104 has received the electronic reference documents, the method 300 proceeds to step 316 at which the provider computing system 104 generates the case dataset including at least a portion of the adverse event data. In some embodiments, at step 316, the provider computing system 104 may store the case dataset or an associated case data object within a repository (e.g., the central document repository 132). Further, the case dataset or the associated case data object may include a link or reference to the electronic reference documents (see FIGS. 6A-6C). In some embodiments, at step 316, the provider computing system 104 may further generate and provide a user interface and associated case page to the user computing device 108 for display. In some embodiments, the case dataset may include information in addition to the adverse event data. For example, the case dataset may include generated case data or case data received from the user computing device 108.

Once the provider computing system 104 has generated the case dataset, the method 300 proceeds to step 320 at which the provider computing system 104 determines if the adverse event is expected or unexpected based on the defined adverse reactions of the reference document(s), the seriousness exclusion(s), and the undefined adverse event action. Steps 320-332 may be understood as being a part of the generating process of step 316 as changes are still occurring within one or more portions of the case dataset. In this regard, it should be understood that step 320 may take place prior or directly prior to step 316 and steps 324-332 may be performed as a part of step 316. For example, the provider computing system 104 may determine whether the adverse event is expected or unexpected and then indicate as such in the case dataset. In some embodiments, the provider computing system 104 may determine whether the adverse event is expected or unexpected for each of the reference documents.

To determine whether the adverse event is expected or unexpected, the provider computing system 104 may first determine whether each adverse event is included as a defined adverse reaction within the respective reference document (e.g., by determining if the reference document includes or identifies the MedDRA term or code associated with the adverse reaction at all). If the adverse event is not listed as a defined adverse reaction, the provider computing system 104 may take the action of the undefined adverse event action (e.g., mark as expected, mark as unexpected, send a notification to the user computing device 108 requesting a manual selection, etc.). In comparison, if the adverse event is listed as a defined adverse reaction, the provider computing system 104 may compare the expectedness cut-off date to the active start date and/or the optional active end date of the defined adverse reaction. If the expectedness cut-off date is (inclusively) between the active start date and the optional active end date or is (inclusively) after the active start date (when there is no optional active end date), the provider computing system 104 may determine the adverse event is expected or unexpected (as indicated on the defined adverse reaction) and proceed to step 324 or 328. If the expectedness cut-off date is outside of the active start date and the optional end date or is before the active start date, the provider computing system 104 may take the action of the undefined adverse event action (e.g., mark as expected, mark as unexpected, send a notification to the user computing device 108 requesting a manual selection, etc.), and proceed to step 324 or 328. In some embodiments, if the adverse event is undefined, the provider computing system 104 may automatically determine the adverse event is expected. In other embodiments, if the adverse event is undefined, the provider computing system 104 may automatically determine the adverse event is unexpected. Inclusively between includes the active start date and the optional active end date, and inclusively after includes the active start date.

In some embodiments, the provider computing system 104 may determine whether each adverse event is expected or unexpected based on the one or more defined adverse reactions of the reference document, the seriousness exclusions of the reference document, the seriousness of each of the adverse events, and/or the undefined adverse event action of the reference document. For example, the reference document may include the adverse event "rash" as an expected defined adverse reaction, but also include a seriousness exclusion of "results in death." Accordingly, if the adverse event is a rash with a seriousness "results in death," the provider computing system 104 may determine the adverse event is unexpected. In another example, the reference document may include an undefined adverse event action of "mark as expected." Accordingly, if the adverse event is not defined by the adverse reactions of the reference document, the provider computing system 104 may determine the adverse event is expected. In some embodiments, if an adverse event corresponds to a seriousness exclusion (i.e., has a seriousness identified by the seriousness exclusion), the provider computing system 104 automatically sets the adverse event to unexpected.

In some embodiments, prior to or after step 320, the provider computing system 104 may determine the listedness of the adverse event, in addition to or separate from the expectedness of the adverse event. As described herein, expectedness may be associated with or applied to an adverse event of a drug or medical product that is currently under investigation or development (e.g., in a clinical study, pre-marketing, etc.), and listedness may be associated with or applied to an adverse event of a drug or medical product that is marketed. In this regard, the primary difference between determining listedness and expectedness may be the reference document from which the provider computing system 104 determines each. For example, to determine listedness, the provider computing system 104 may receive and analyze the company core datasheet or the IB of the marketed medical product or drug. In some embodiments, the provider computing system 104 may determine listedness and/or expectedness from any of the reference documents.

If at step 320, the provider computing system 104 determines the adverse event is expected, the method 300 proceeds to step 324 at which the provider computing system 104 indicates the adverse event is expected in the case dataset. In some embodiments, at step 324, the provider computing system 104 further indicates on a graphical user interface (GUI), that is displayed on the user computing device 108, that the adverse event is expected in the case dataset (e.g., on a case page 600, see FIGS. 6A-6B). As described herein, the provider computing system 104 may indicate an adverse event is expected in one or more ways such as by specifically emphasizing, marking, (e.g., with an asterisk and a footnote, with a number and a footnote, with another specific character and a footnote, etc.) or highlighting the expected adverse event in comparison to the unexpected adverse events. In another example, the provider computing system may indicate an adverse event is expected by stating "expected" next to the adverse event and the respective reference document.

In comparison, if at step 320 the provider computing system 104 determines the adverse event is unexpected, the method 300 proceeds to step 328 at which the provider computing system 104 indicates the adverse event is unexpected in the one or more sections of the aggregate report. In some embodiments, at step 328, the provider computing system 104 further indicates on a graphical user interface (GUI), that is displayed on the user computing device 108, that the adverse event is unexpected in the case dataset (e.g., on a case page 600, see FIGS. 6A-6C). As described herein, the provider computing system 104 may indicate an adverse event is unexpected in one or more ways such as by specifically emphasizing, marking, (e.g., with an asterisk and a footnote, with a number and a footnote, with another specific character and a footnote, etc.) or highlighting the expected adverse event in comparison to the unexpected adverse events. In another example, the provider computing system may indicate an adverse event is unexpected by stating "unexpected" next to the adverse event and the respective reference document.

In some embodiments, steps 320-328 may be repeated by the provider computing system 104 for each of the reference documents. For example, the provider computing system 104 may determine if the adverse event is expected in each of the reference documents received at step 312. In this regard, the provider computing system 104 may determine if the adverse event is expected for a first reference document (e.g., an IB) and indicate or mark the adverse event as such (e.g., at step 324 or 328). Then, the provider computing system 104 may determine if the adverse event is expected for a second reference document (e.g., a SmPC) and indicate or mark the adverse event as such (e.g., at step 324 or 328). Steps 320-328 may be repeated for any number of reference documents.

After either or both of steps 324 and 328, the method 300 proceeds to step 332 at which the provider computing system 104 determines one or more submission timeframes for the case dataset based on the reference source document(s), the expectedness of the adverse event, and/or the seriousness of the adverse event. The submission timeframe may be a period of time within which the case dataset is to be submitted to a health authority. For example, the submission timeframe may be a number of days, hours, weeks, or months. In one example, the submission timeframe may be 5, 10, 15, 20, or 30 days. In another example, the submission timeframe may be relative (e.g., within the end of the month, within the end of next month, etc.). In some embodiments, at step 332, the provider computing system 104 may further determine a submission address or sender to which the submission is to be transmitted based on the reference source document, the expectedness of the case dataset, and any product registrations of the case datasheet. For example, if the provider computing system 104 receives case data indicating the medical product is registered in the U.S., Canada, and Germany, the provider computing system 104 may determine the case datasheet is to be submitted to the FDA, Health Canada, and the EMA.

To determine the submission timeframe for the case dataset, the provider computing system 104 may analyze the expectedness for each of the reference documents, the type of reference document, and the seriousness of the adverse event. For example, if the adverse event is associated with a study, the provider computing system 104 the provider computing system 104 may determine the submission timeframe based on the expectedness of the IB, the submission address, and the seriousness of the adverse event. If the adverse event is expected and not serious, based on the IB, the provider computing system 104 may determine no submission is required. If the adverse is expected and serious, based on the IB, the provider computing system 104 may determine a submission is required within 30 days. If the adverse is unexpected and serious, based on the IB, the provider computing system 104 may determine a submission is required within 15 days.

In another example, if the medical product is not associated with a study, the provider computing system 104 may determine the submission timeframe based on the expectedness of any region-specific reference documents, the company core datasheet, the submission address, and/or the seriousness of the adverse event. If the adverse event is expected and not serious, based on the company core datasheet and/or the region-specific reference documents, the provider computing system 104 may determine no submission is required. If the adverse is expected and serious, based on the company core datasheet and/or the region-specific reference documents, the provider computing system 104 may determine a submission is required within 30 days. If the adverse is unexpected and serious, based on the company core datasheet and/or the region-specific reference documents, the provider computing system 104 may determine a submission is required within 15 days. In some embodiments, the region-specific reference document may take precedence over the company core datasheet such that if a region-specific reference document is available, the submission timeframe for a specific country is based on the expectedness region-specific reference document and not the company core datasheet.

Additionally, the submission timeframe may be determined based on the submission address (i.e., the country or region the submission is to be made in). For example, the provider computing system 104 may determine a serious unexpected submission to the EMA has a submission timeframe of 10 days, but the same submission to the FDA has a submission timeframe of 15 days.

Once the provider computing system 104 has determined the one or more submission timeframes, the method 300 proceeds to step 336 at which the provider computing system 104 outputs or transmits the case dataset within the one or more submission timeframes. In some embodiments, the provider computing system 104 may output the first case dataset to at least one of a health agency computing system 112 or the user computing device 108. The health agency computing system 112 may be associated with a health authority or agency indicated by the submission address. In one example, the provider computing system 104 may output the case dataset to a first health agency computing system 112 (e.g., associated with the FDA) within a first submission timeframe, and output the case dataset to a second health agency computing system (e.g., associated with the EMA) within a second submission timeframe. In some embodiments, the case dataset is output as an E2B XML file.

In some embodiments, prior to outputting the case dataset, the provider computing system may generate a submission for each of the submission timeframes. The submission may include or indicate the submission address (e.g., the FDA gateway, the EMA gateway, etc.), the respective submission timeframe, a submission data type or file type (e.g., E2B (R2) XML, E2B (R3) XML, etc.), adverse event or case details (e.g., seriousness, adverse event code or type (e.g., Rash)), the expectedness of the adverse event, and the like. FIG. 6B, shows multiple submissions that are generated by the provider computing system 104 and provided to the user computing device 108 for display and selection of submission.

Referring now to FIGS. 4-6C, user interfaces shown and displayed to the user of the user computing device 108 during the methods 200 and/or 300 are shown, according to example embodiments. As described herein, the user interfaces of FIGS. 4-6C may be one or more of web interfaces generated by the provider computing system 104 and rendered by the user computing device 108 as part of a web application or graphical user interfaces downloaded and generated by the user computing device 108 as part of a software application (e.g., a mobile application, etc.). Further, the user interfaces shown on FIGS. 4-6C allow for communication between the user and the provider computing system 104 via the user computing device 108 (specifically via the I/O circuit 162). Through interaction with the various user interfaces, the user may provide user input, feedback, and other data requested by the provider computing system 104. In this regard, it should be understood that each interaction described herein by the user with the user interfaces of FIGS. 3-4 may be provided to the user computing device 108 and then transmitted to the provider computing system 104 and that each action described herein as occurring to the user computing device 108 (e.g., navigating to a certain page, generating a popup, etc.) may be performed by the provider computing system 104.

Figure 4:
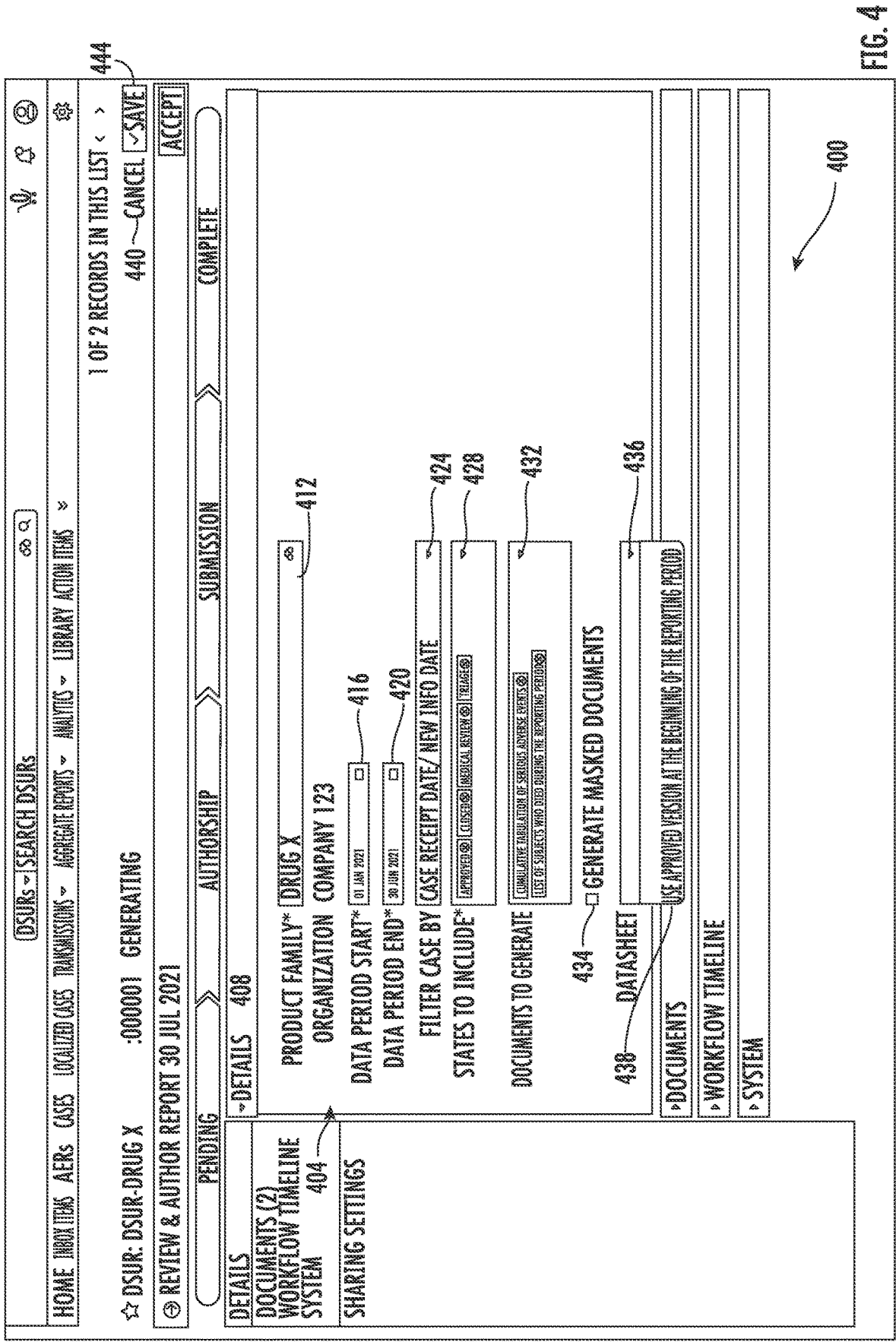
FIG. 4 is an illustration of some aspects of a user interface generated by the adverse reaction expectedness monitoring and analyzation system of FIG. 1 to generate and receive a request to generate an aggregate report, according to an example embodiment.

Referring now to FIG. 4, a request generation page 400, which can be displayed on a display of the I/O circuit 162 of the user computing device 108, is shown. In general, the request generation page 400 provides the user with an interface to generate and specify the portions of the request (e.g., the associated medical product, the associated clinical trial/study, the period start date, the period end date, etc.). As shown, the request generation page 400 includes a request details section 404, a cancel button, and a save or submit button 444.

The request details section 404 allows the user to manage and set details of the request such as the associated medical product, the organization, one or more case filters, sections of the aggregate report to generate, etc. As shown, the request details section 404 includes a toggleable header 408, a medical product field 412, a reporting period start date field 416, a reporting period end date field 420, a filter case drop-down box 424, a case states drop-down box 428, a sections to generate drop-down box 432, a masked document checkbox 434, and an expectedness cut-off date drop-down box 436. The toggleable header 408 is a selectable header or button that, when selected, hides or displays the request details section 404 (depending on if the request details section 404 is currently hidden or displayed).

The medical product field 412 is a selectable and editable text field through which the user of the user computing device 108 can edit or initially set the associated medical product of the request. In some embodiments, if the user selects the binocular portion of the medical product field 412, the user can search through the central document repository 132 (e.g., by sending a search request to the provider computing system 104) or a medical product data repository (not shown) for saved medical products (i.e., that have been cited or used in cases or other documents previously). By selecting the specific medical product or entering a specific medical product in the medical product field 412, the user may then set the associated medical product for which the aggregate report and the request is associated with.

The reporting period start date field 416 and the reporting period end date field 420 are selectable and editable text fields through which the user of the user computing device 108 can edit or initially set the reporting period start date and the reporting period end date of the request, respectfully.

The filter case drop-down box 424 is a selectable drop-down box that, when selected, drops down one or more selectable case filters or filter options. In response to dropping down the filter options, the user may select one or more of the status options to decide the order in which the cases and associated adverse events are listed on the aggregate report. In this regard, if the user were to select the "case receipt date" filter option, the provider computing system 104 may receive a notification indicating as such and generate the one or more sections of the aggregate report with the adverse events listed or filtered in the order specified by the filter optional (e.g., in order of date received, etc.). Likewise, the case states drop-down box 428 is a selectable drop-down box that, when selected, drops down one or more selectable case state options. In response to dropping down the case state options, the user may select one or more of the case state options (e.g., approved, closed, medical review, and/or triage) to decide which cases and associated adverse events should be included in the aggregate report. In this regard, if the user were to only select the "approved" and "closed" case state options, the provider computing system 104 would only retrieve or receive cases and associated adverse events that were in the approved (i.e., verified as correct but not transmitted to a health agency computing system 112 (e.g., the FDA electronic submissions gateway)) or closed (i.e., verified as correct and transmitted to a health agency computing system 112 (e.g., the FDA electronic submissions gateway)) states from the central document repository 132 to be included in the aggregate report and analyzed for expectedness.

Similarly, the sections to generate drop-down box 432 is a selectable drop-down box that, when selected, drops down one or more sections (i.e., documents) options to be generated by the provider computing system 104 and included in the aggregate report. In response to dropping down the document options, the user may select one or more of the document options to decide which sections or documents of the aggregate report the provider computing system 104 is to generate. In this regard, if the user were to select the "cumulative tabulation of serious adverse events" document option, the provider computing system 104 may receive a notification indicating as such and generate a cumulative tabulation indicating each SAR that took place within the reporting period based on the received cases. In some embodiments, the sections to generate drop-down box 432 includes a "cumulative tabulation unexpected serious adverse events" document option. In other embodiments, the provider computing system 104 may automatically indicate or identify the unexpected adverse events in any of the documents or sections of the aggregate report generated by the provider computing systems.

The masked document checkbox 434 is a selectable checkbox that, when checked, indicates one or more portions of the aggregate report (i.e., private health information (PHI), personal information, identifying information, sections of the aggregate report, etc.) are to be masked in the display of the aggregate report, but which may be stored in the central document repository 132 and transmitted or provided by the provider computing system 104 to a health agency computing system 112 (e.g., the FDA electronic submissions gateway). For example, if the provider computing system 104 receives a request indicating it is to generate a listing of subjects who died during the reporting period and generate masked documents (as indicated by a checked masked document checkbox 434), the provider computing system 104 may generate the listing of subjects who died during the reporting period. Further, the provider computing system 104 may mask the personal or identifiable patient data such that when a user (e.g., of the user computing device 108) attempts to view the listing of subjects who died during the reporting period of the aggregate report, the user only sees masked characters or masked data (e.g., "******" instead of "Tom Smith"). In this regard, the patients identifiable and PHI is protected and not able to be viewed by the user. In some embodiments, the provider computing system 104 masking the documents may include encrypting the documents (and/or the aggregate report) and then storing each within the central document repository 132**.

The expectedness cut-off date drop-down box 436 is a selectable drop-down box that, when selected, drops down one or more expectedness cut-off date options 438 through which the user can set the expectedness cut-off date. In response to dropping down the document options, the user may select the one or more expectedness cut-off date options 438 to decide which expectedness cut-off date the provider computing system 104 should use in deciding expectedness. In this regard, if the expectedness cut-off date drop-down box 436 may include a variable number of expectedness cut-off date options 438 based on the aggregate report type. For example, if the aggregate report to be generated is a DSUR, the expectedness cut-off date drop-down box 436 may only include a single expectedness cut-off date optional 438 (e.g., "use approved version at the beginning of the reporting period") based on the aggregate report being a DSUR (and as defined in the E2F DSUR guidance). In comparison, if the aggregate report is a PSUR, the expectedness cut-off date drop-down box 436 may only include two expectedness cut-off date options 438 (e.g., "use approved version at the beginning of the reporting period" and "use approved version at the end of the reporting period") based on the aggregate report being a PSUR. In this regard, the provider computing system 104 may determine one or more expectedness cut-off dates (as described with regard to step 216) and provide them to the user computing device 108 for display and selection in the expectedness cut-off date drop-down box 436. Once the user selects the document option, the preferred or correct expectedness cut-off date optional 438, the provider computing system 104 may receive the request indicating as such and determine expectedness based on expectedness cut-off date optional 438 selected by the user of the user computing device 108.

The cancel button 440 is a selectable button that, when selected, cancels the generation of the request (deletes or does not save the data the user provided via the request generation page 400) and may navigate the user of the user computing device 108 to another page (e.g., the page the user was previously on). Similarly, the save button 444 is a selectable button that, when selected, causes the user computing device 108 to generate the request to generate the aggregate report including all the data the user provided via the request generation page 400 and provide the request to the provider computing system 104 to generate the aggregate report (or sections thereof). In some embodiments, the provider computing system 104 may save the request and data included in the request in the central document repository 132.

Figure 5A:
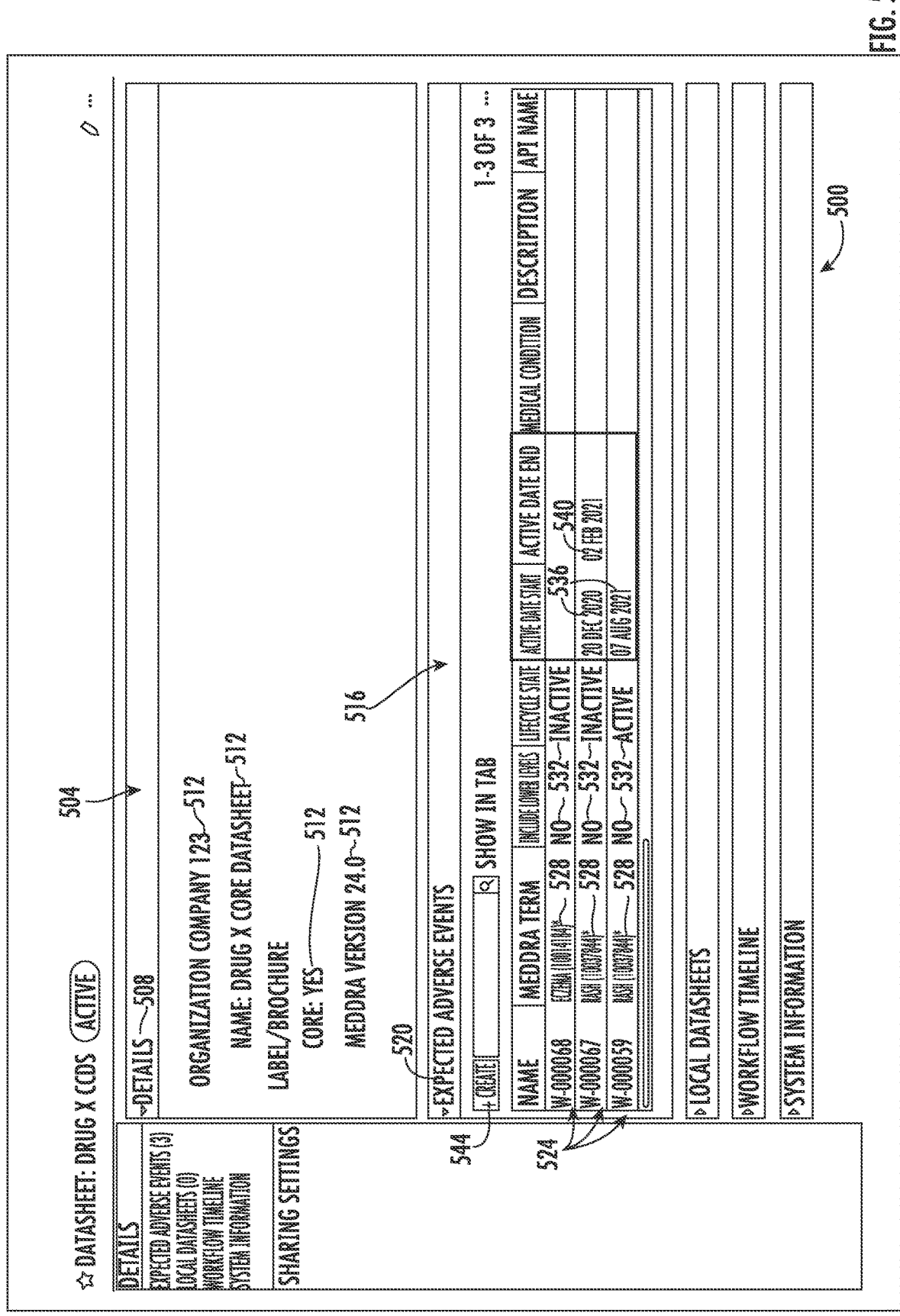
FIGS. 5A-5C are illustrations of some aspects of a user interface generated by the adverse reaction expectedness monitoring and analyzation system of FIG. 1 to monitor expectedness in a reference document, according to an example embodiment.
Figure 5B:
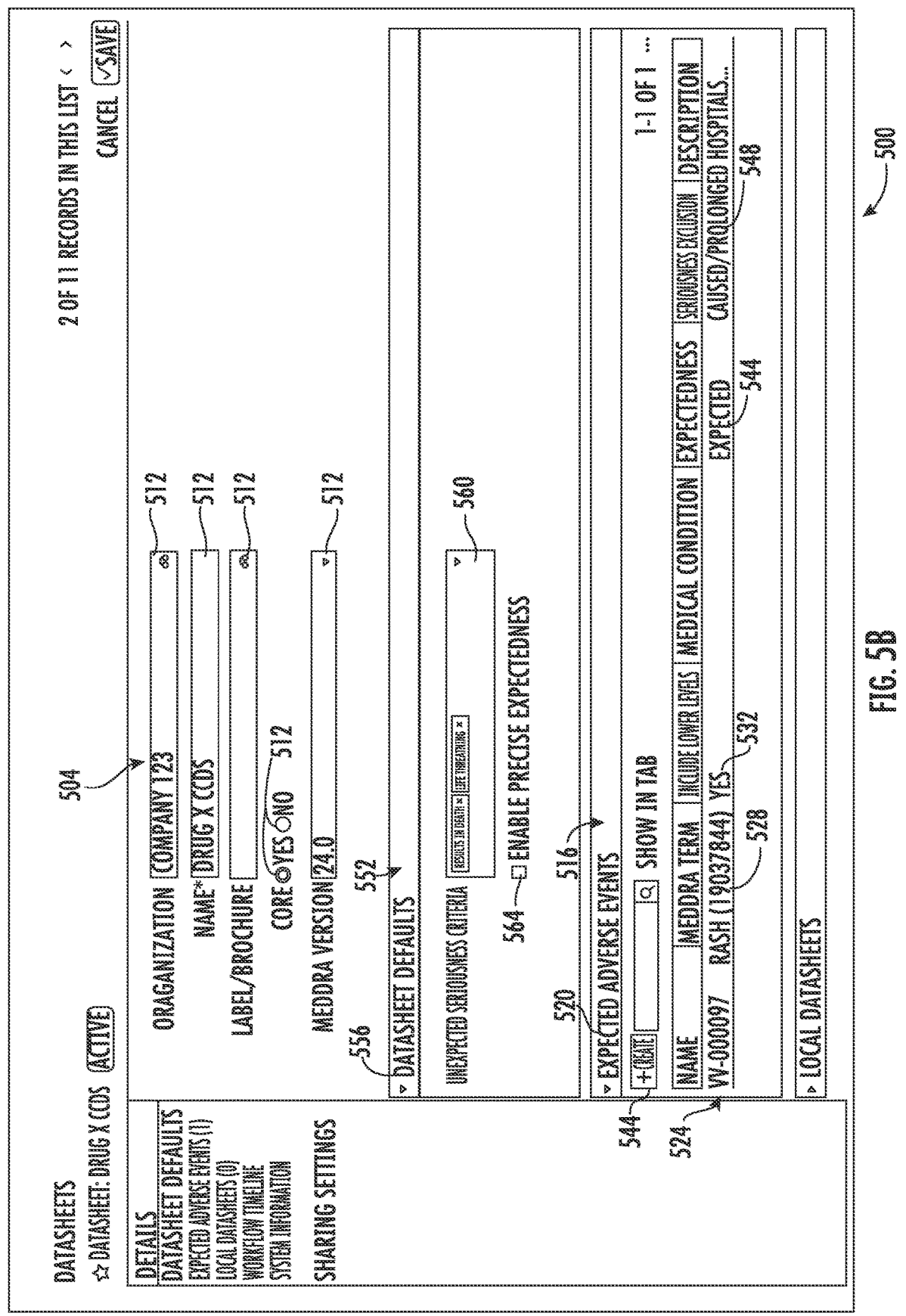
Figure 5C:
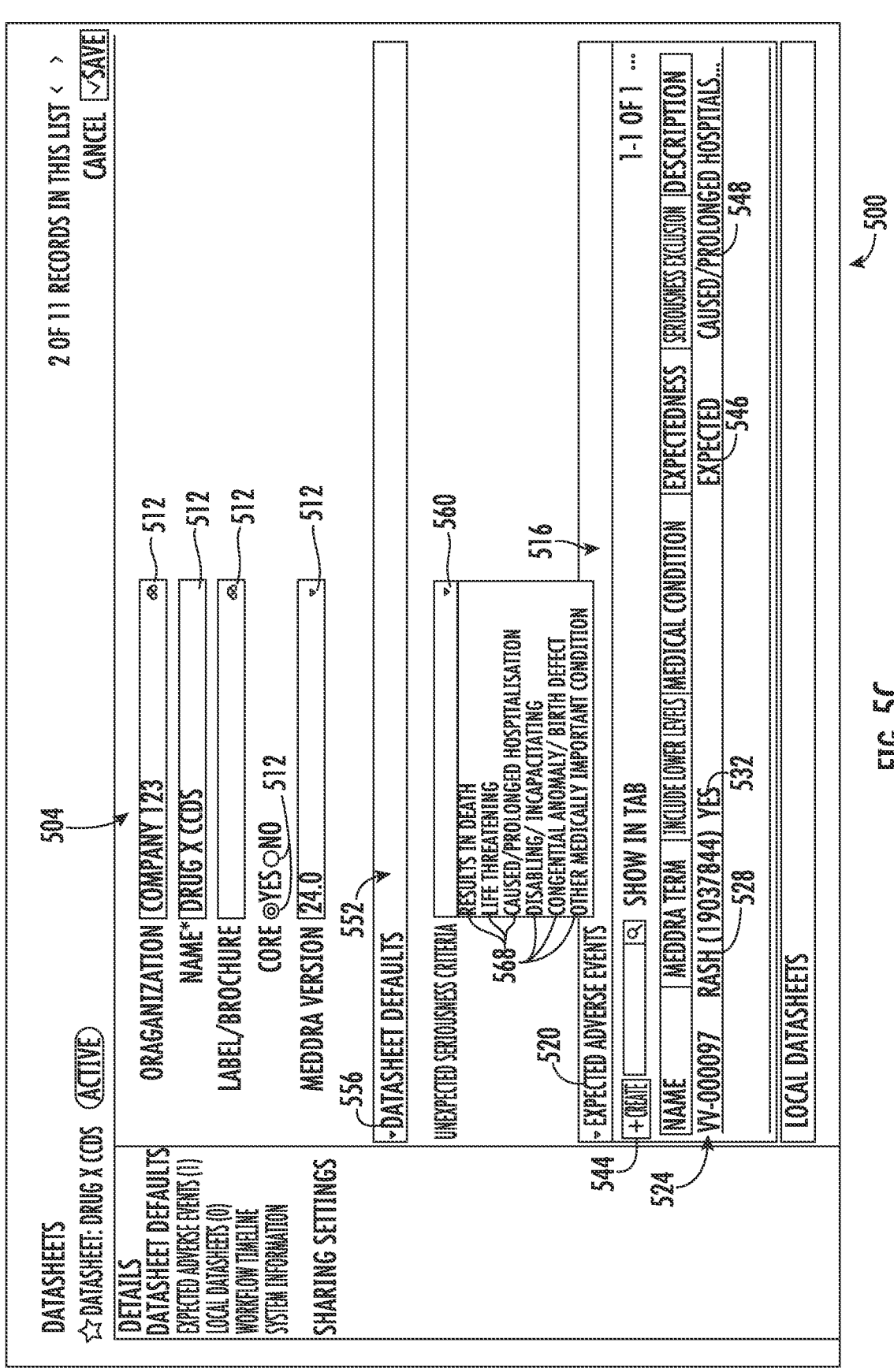

Referring now to FIGS. 5A-5C, a company core data sheet page 500, which can be displayed on a display of the I/O circuit 162 of the user computing device 108, is shown. In general, the core data sheet page 500 provides the user with an interface to view and manage an organizations company core datasheet (e.g., a CCSI) for a specific medical product. While not shown, the provider computing system 104 may generate and provide a similar page (e.g., reference document page(s)) for other reference documents including an investigational brochure page, a region-specific labelling page for each different region-specific labelling document, and the like. In this regard, the provider computing system 104 may provide one or more portions of the reference document or reference document data associated with the reference document (e.g., the company core data sheet) to the user computing device 108 to enable display of the company core data sheet page 500 or the other reference document pages on the display of the I/O circuit 162. As shown, the core data sheet page 500 includes a core data sheet details section 504, a defined adverse events or reactions section 516, and a datasheet settings section 552.

The core data sheet details section 504 provides the user of the user computing device 108 with an interface to manage and set details of the core data sheet such as the associated medical product, the organization, the name of the core data sheet, the version of the MedDRA in use, and the like. As shown, the core data sheet details section 504 includes a toggleable header 508 and multiple of fields 512 such as an organization field 512, a name field 512, a core field 512, a label/brochure field 512, and a MedDRA version field 512. The toggleable header 508 is a selectable header or button that, when selected, hides or displays the core data sheet details section 504 (depending on if the core data sheet details section 504 is currently hidden or displayed).

The fields 512 are selectable and editable text fields or buttons through which the user of the user computing device 108 can edit or initially set the organization, the name of the core data sheet, the label or brochure associated with the company core datasheet, whether the data sheet is the core data sheet, and the MedDRA version in use.

The defined adverse events or reactions section 516 allows the user to set and manage one or more defined adverse events or reactions associated with the medical product and to be included in the company core datasheet and provide the defined adverse events or reactions to the provider computing system 104 from the user computing device 108. As shown, the defined adverse events or reactions section 516 includes a toggleable header 520, multiple defined adverse reaction representations 524, and a create button 544. The toggleable header 520 is a selectable header or button that, when selected, hides or displays the defined adverse events or reactions section 516 (depending on if the defined adverse events or reactions section 516 is currently hidden or displayed).

Each defined adverse reaction representation 524 represents an adverse event that is expected or unexpected with use of the associated medical product (e.g., Drug X) and is included in the company core datasheet of the medical product and through which expectedness is determined by the provider computing system 104 (as discussed with regard to the method 200). As shown, each defined adverse reaction representation 524 includes a MedDRA term field or link 528, multiple fields 532, an active start date 536, an optional active end date 540, an expectedness field 546, and a seriousness exclusion field 548.

The MedDRA term field or link 528 is a selectable and/or editable field or link that indicates the MedDRA term or code associated with the adverse event. Further, the link 528 is selectable such that when the user selects the link 528, they may be navigated to a MedDRA term page (not shown) that provides additional details pertaining to the MedDRA term and code. Similarly, the multiple fields 532 are text fields that provide data pertaining to the defined adverse reaction such as whether the adverse event is currently active (i.e., expected or unexpected) or inactive or whether the MedDRA term includes lower MedDRA levels (as defined by the MedDRA hierarchy).

The active start date 536 is a selectable and editable field that represents the date on which the adverse reaction represented by the defined adverse reaction representation 524 is considered expected or unexpected (as defined by the expectedness field 546) and the optional active end date 540 is the date after which the adverse reaction represented by the defined adverse reaction representation 524 is no longer considered defined (i.e., expected or unexpected). If a defined adverse reaction representation 524 includes a start date 536 but does not include an optional active end date 540, the defined adverse reaction is still active and considered expected or unexpected after the active start date 536. In comparison, if the defined adverse reaction representation 524 includes a start date 536 and an optional active end date 540, the defined adverse reaction is still no longer active but is considered expected or unexpected between the two dates.

The expectedness field 546 is a selectable and editable field that indicates or represents the expectedness of the defined adverse event or reaction 524. For example, the expectedness may be set to "expected" or "unexpected." When the expectedness field 546 set to expected, the provider computing system 104 may determine the expectedness of any adverse event (matching the MedDRA term 528) and occurring between the active start date 536 and optional active end date 540 as being expected based on the defined adverse reaction 524. Similarly, when the expectedness field 546 is set to unexpected, the provider computing system 104 may determine the expectedness of any adverse event (matching the MedDRA term 528) and occurring between the active start date 536 and optional active end date 540 as being unexpected based on the defined adverse reaction 524. In this regard, the expectedness field may define the expectedness of the defined adverse reaction 524. For example, the defined adverse reactions described herein may include an expectedness field indicating whether the defined adverse reaction is expected or unexpected.

The seriousness exclusion field 548 is a selectable and editable field that indicates or represents the seriousness exclusion of the defined adverse event or reaction 524. In this regard, the seriousness exclusion field 548 may be set to one or more combinations of: "Results in death," "Life Threatening," "Caused/prolonged hospitalization," "Disabling/incapacitating," "Congenital anomaly/birth defect" or "Other medically important condition" (see FIG. 5C.), indicating one or more combinations of seriousness which override the expectedness of the adverse reaction 524. For example, the seriousness exclusion field 548 may be set to "Results in death" or "Life Threatening". Then, in response to the provider computing system 104 receiving an adverse reaction 524 or reference document indicating as such, the provider computing system 104 may determine an adverse event is expected or unexpected based on the seriousness of the adverse event, the seriousness exclusion identified by the seriousness exclusion field 548, and the expectedness field 546 of the adverse reaction 524. In some embodiments, if an adverse event corresponds to a seriousness exclusion (i.e., has a seriousness identified by the seriousness exclusion), the provider computing system 104 automatically sets the adverse event to unexpected. In this regard, the seriousness exclusions may be set specific to each adverse reaction 524.

While not shown, the define adverse reaction 524 may further include an undefined adverse event or reaction action field, which may be a selectable and editable field that indicates or represents the action the provider computing system 104 is to take if the adverse reaction is undefined (e.g., is no longer active, is outside the active start date 536 and the optional active end date 540, etc.). For example, the undefined adverse event or reaction action field may be set to unexpected or mark as unexpected. Then, in response to the provider computing system 104 receiving the adverse reaction including the undefined adverse event or reaction action field as well as an adverse event matching the adverse reaction 524, the provider computing system 104 may determine if the present date or the expectedness cut-off date of an aggregate report is within the active start date 536 and the optional active end date 540 of the adverse reaction 524. If it is not, the provider computing system 104 may mark or determine the adverse event is unexpected. In this regard, the undefined adverse event or reaction action may be set specific to each adverse reaction 524.

The create button 544 is a selectable button that, when selected, causes the user computing device 108 to generate a new defined adverse reaction representation 524. The new defined adverse reaction representation 524 may be blank or empty (e.g., each field and portion of the defined adverse reaction representation 524 may be empty and the representation 524 may be inactive) until the user edits each and provides the MedDRA term or code in the MedDRA term field or link 528, fills out the fields, and provides an active start date 536. To inactivate a defined adverse reaction representation 524 the user may edit the optional active end date 540 to provide an end date.

The defined adverse events or reactions section 516 provides the core data sheet page 500 and the user with a way to manage defined adverse reactions without having to constantly version the core data sheet itself and therefore requires less memory. Because the core data sheet for a specific medical product can have a large number of defined adverse reactions over the lifetime of the medical product, core data sheets can go through many changes. If the provider computing system 104 were to version the core data sheet (e.g., create and store a new copy of the core data sheet) within the central document repository 132 each time an adverse reaction was modified from expected to unexpected or vice versa, the central document repository 132 may store a large quantity for each core data sheet for each medical product. In comparison, the provider computing system 104 and the core data sheet page 500 does not version the entire core data sheet, but instead adds a defined adverse reaction representation 524 with an active start date 536 and an optional active end date 540 for each new defined adverse reaction, which is one piece of data compared to an entire core data sheet. By doing so, the provider computing system 104 only stores a single copy of the core data sheet for each medical product within the central document repository 132 with changes being made to the defined adverse events of the core data sheet, which saves on memory for the provider computing system 104 and the central document repository 132 and processing power for the provider computing system 104 by not having to repeatedly replicate the core data sheet.

The datasheet settings or defaults section 556 allows and provides the user an interface to set and manage one or more settings or default settings associated with the respective datasheet (e.g., the company core datasheet) and provide the settings to the provider computing system 104 from the user computing device 108. As shown, the datasheet settings section 556 includes a global unexpected seriousness criteria field and/or drop-down box 560 and an enable precise expectedness button or field 564.

The global seriousness exclusion drop-down box 560 is a selectable and editable drop-down box that, when selected, drops down one or more seriousness exclusion options 568 (see FIG. 5C) to select and set seriousness exclusions for the reference document as a whole. In this regard, the user of the user computing device 108 may select or click any combination of the seriousness exclusion options 568. The seriousness exclusions may be applied to each of the expected adverse reactions 524 included within the company core datasheet page 500. For example, the seriousness exclusion drop-down box 560 may be set to "Results in death" or "Life Threatening". Then, in response to the provider computing system 104 receiving a reference document indicating as such, the provider computing system 104 may determine an adverse event is expected or unexpected based on the seriousness of the adverse event, the seriousness exclusion identified by the seriousness exclusion drop-down box 560. In this regard, the seriousness exclusions may be set generally for the reference document a s a whole.

The enable precise expectedness button or field 564 is a selectable and editable field or button that, when selected (i.e., checked), enables the undefined adverse event or reaction action field of each adverse reaction 524. In this regard, the enable precise expectedness button 564 is checked, the provider computing system 104 may take the action defined by the undefined adverse event or reaction action field when the adverse reaction is not active. In some embodiments, the datasheet settings section 556 further includes a global undefined adverse event or reaction action field through which the user of the user computing device 108 can set and provide a reference document specific undefined adverse event action. For example, through interaction with the global undefined adverse event or reaction action field, the user may set the undefined adverse event action to require manual selection of expectedness for each undefined adverse event or reaction. Then, in response to receiving a reference document indicating as such, the provider computing system 104 may generate and provide a notification to the user computing device 108 requesting manual selection of expectedness (i.e., expected or unexpected) for any undefined adverse events. In response to providing the notification, the provider computing system 104 may receive an indication of the expectedness for the undefined adverse events from the user computing device 108.

Figure 6A:
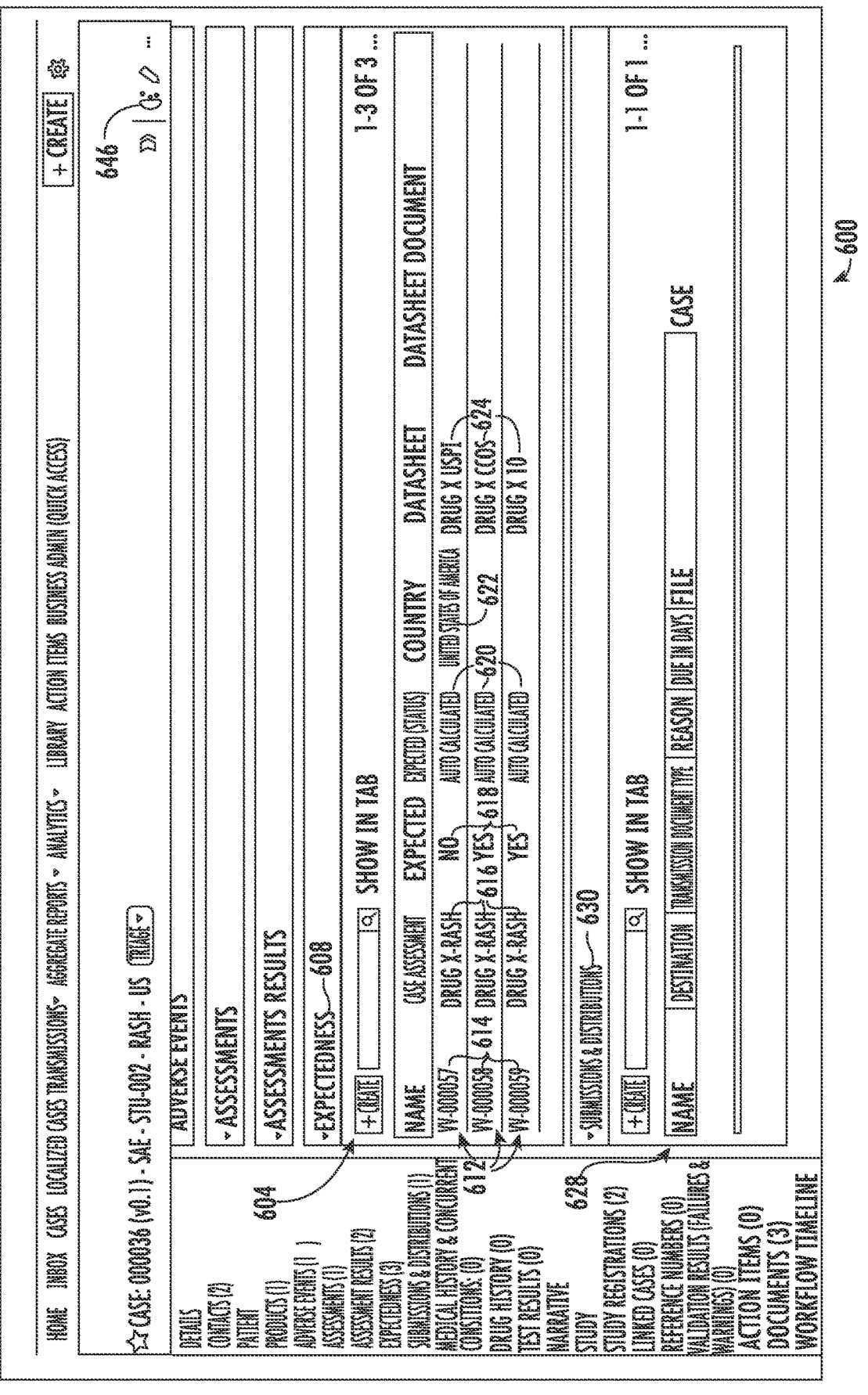
FIGS. 6A-6C are illustrations of some aspects of a user interface generated by the adverse reaction expectedness monitoring and analyzation system of FIG. 1 to indicate expectedness in a case, according to an example embodiment.
Figure 6B:
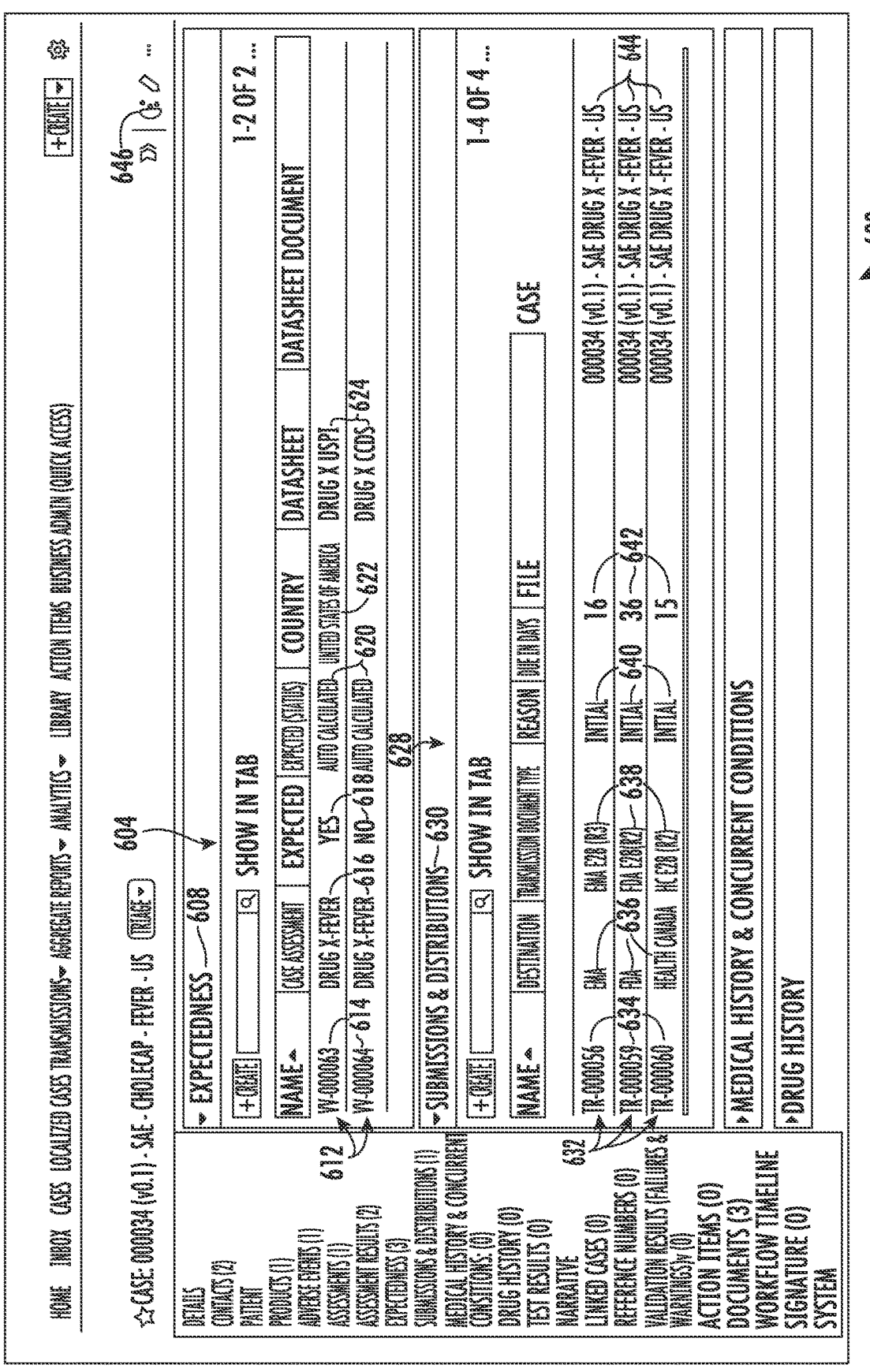
Figure 6C:
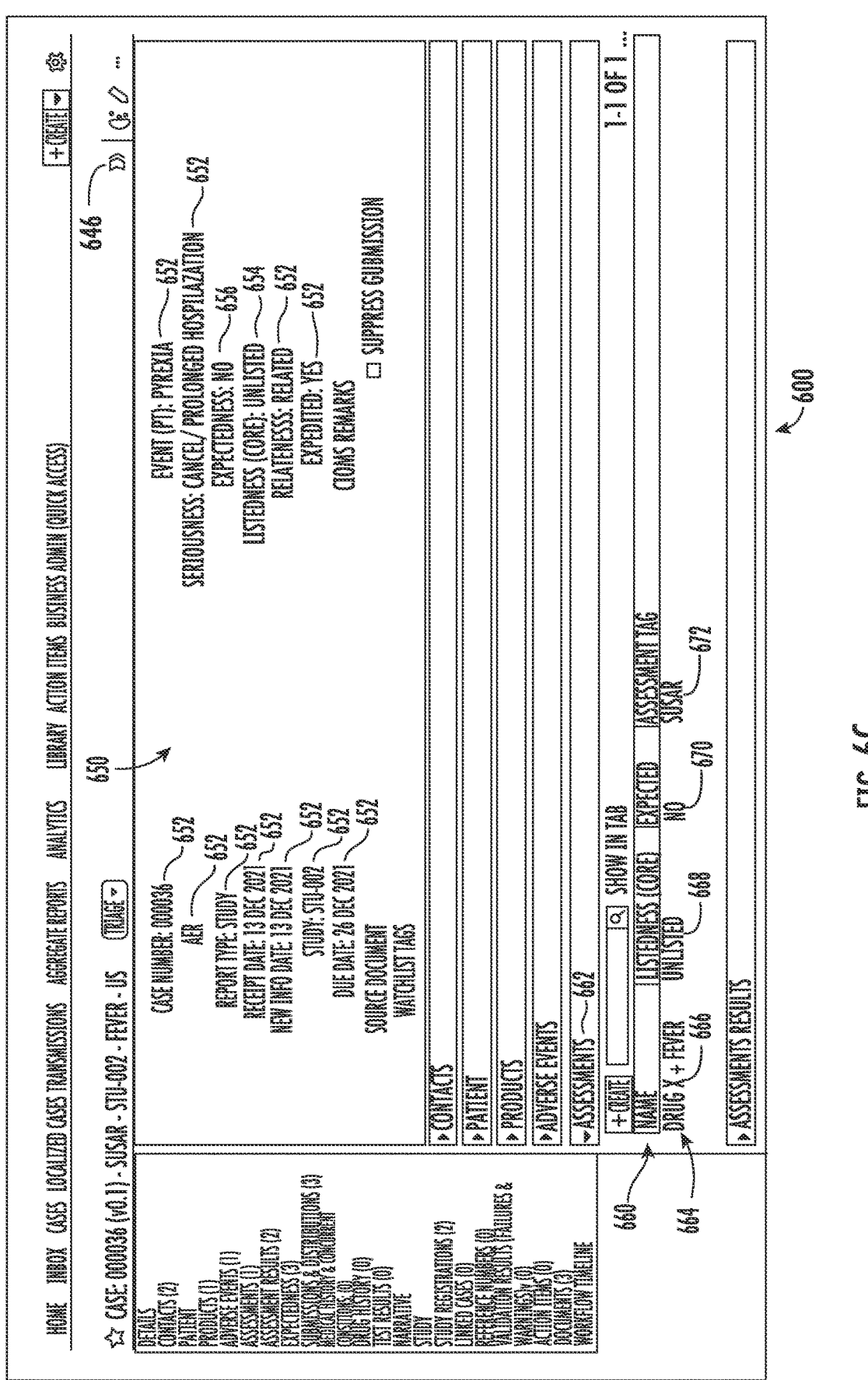

Referring now to FIGS. 6A-6C, a case page 600, which can be displayed on a display of the I/O circuit 162 of the user computing device 108, is shown. In general, the case page 600 provides the user computing device 108 with an interface to view and manage the case dataset for a specific case dataset (e.g., the case dataset generated in the method 300) and provide any changes to the case dataset to the provider computing system 104. For example, via the case page 600, the user may provide additional or replacement case data to the user computing device 108, which may provide the additional or replacement case data to the provider computing system 104 to store as a part of the case dataset. In this regard, the provider computing system 104 may provide case data associated with the case dataset to the user computing device 108 to enable display of the case page 600 on the display of the I/O circuit 162. Further, it should be understood that while FIGS. 6A-6C show the same case page 600, it should be understood FIGS. 6A and 6C are associated with a different case dataset than FIG. 6B. FIGS. FIGS. 6A and 6C represent a case dataset associated with a study (as indicated by the portion of the case title "STU-002", and FIG. 6B represents a case dataset associated with a marketed medical product. As shown, the case page 600 includes an expectedness section 604, a submissions section 628, a generate and/or process submission button 646, a case overview section 650, and an assessment or listedness section 660.

The expectedness section 604 provides the user of the user computing device 108 with an interface to manage and determine the expectedness for the adverse event associated with the case dataset of the case page 600. As shown, the expectedness section 604 includes a toggleable header 608 and one or more expectedness representations 612. The toggleable header may be similar or the same as the toggleable header 408. In some embodiments, the expectedness section 604 may include an expectedness representation 612 for each of the reference documents associated with the medical product or study of the case dataset (e.g., the reference documents determined and received at steps 308-312).

Each expectedness representation 612 represents or relates to a determination of expectedness (e.g., at step 320) for a reference document and the adverse event associated with the case dataset associated with the case page 600. In this regard, the provider computing system 104 may provide the expectedness of the adverse event, the reference document, the reference document used in determining expectedness, and the like (e.g., as a part of the case data) to the user computing device 108 for display or representation as an expectedness representation 612. As shown, each expectedness representation 612 includes a name field or link 614, a case assessment field or link 616, an expectedness field 618, a country or region field 622, and a reference document field 624. The name field or link 614 is a selectable and/or editable field or link that indicates a name of the expectedness representation 612 (e.g., to specify each). In some embodiments, the name field or link 614, when selected, navigates the user computing device 108 to a defined adverse reaction page (not shown) including details about the defined adverse reaction used to make the expectedness determination. Likewise, the case assessment field or link 616 is a selectable and/or editable field or link that, when selected, navigates the user computing device to an assessment page or the assessment section 660 including details on the assessment of the adverse event.

The expectedness field 618 is a field that represents or indicates the expectedness of the adverse event associated with the case dataset of the case page 600 as well as the data that was used in making the determination (e.g., the reference document). For example, the provider computing system 104 may provide the expectedness of the adverse event f to the user computing device 108 for display and indication in the expectedness field 618. Similarly, the reference document field 624 is a field that represents or indicates the reference document used to determine the expectedness of the expectedness field 618 associated with the case dataset of the case page 600. For example, the provider computing system 104 may provide the reference document or an indication of the reference document to the user computing device 108 for display and indication in the reference document field 624. Lastly, the country or region field 622 is a field that represents or indicates the country or region associated with the reference document of the reference document field 624. For example, the USPI of drug x is specific to the country United States of America. Reference documents that are not region or country specific are do not include a country or region in the country or region field 622.

In the case shown on FIGS. 6A and 6C, the provider computing system 104 determined and received three reference documents at steps 308-312 including an IB for drug x, a company core datasheet for drug x, and a USPI for drug x. Then, when determining expectedness for each at step 320, the provider computing system 104 determined the adverse event was expected based on the defined adverse reactions of the IB and the company core datasheet, but unexpected based on the defined adverse reactions of the USPI.

In FIGS. 6A and 6C, the case dataset and the adverse event (rash) is associated with a study (e.g., Study 002). Further, as shown, the provider computing system 104 has determined the expectedness for the adverse event is expected based on the IB and the company core datasheet but unexpected based on the USPI. As a result, the provider computing system 104 has determined that no submissions are required based on the adverse event being expected in the IB. In comparison, in FIG. 6B, the case dataset and the adverse is not associated with a study. Further, as shown, the provider computing system 104 has determined the expectedness for the adverse event is unexpected based on the company core datasheet but expected based on the USPI. As a result, the provider computing system 104 has determined that three submissions are required for the case dataset based on the adverse event being unexpected in the company core datasheet, the seriousness of the adverse event, and the product registrations of the medical product (one with the FDA, one with the ESA, and one with Health Canada). Further, the provider computing system 104 has determined the submission timeframe for the EMA and Health Canada is 15 days based on the unexpectedness in the company core datasheet and the submission address, but the submission timeframe for the FDA is 30 days based on the unexpectedness in the company core datasheet, the expectedness in the USPI, and the submission address. In this regard, the provider computing system 104 may take the region-specific reference documents into consideration when determining the submissions and associated submission timeframes for non-study cases and not take the region-specific reference documents into consideration when determining the submissions and the associated submission timeframes for study cases.

Referring now to FIG. 6B, the submissions section 628 provides the user of the user computing device 108 with an interface to manage and electronically transmit submissions associated with the case dataset. As shown, the submissions section 628 includes a toggleable header 630 and one or more submissions or submission representations 632. The toggleable header 630 may be similar or the same as the toggleable header 408. In some embodiments, the submissions section 628 may include a submission representation 632 for each of the regions or countries the medical product is registered in.

Each submission representation 632 represents or relates to a submission associated with the case dataset of the case page 600. In this regard, the provider computing system 104 may provide the submission address, the file type of the submission, the submission timeframe, and the like (e.g., as a part of the submission) to the user computing device 108 for display or representation as a submission representation 632. As shown, each submission representation 632 includes a name field or link 632, a submission destination field or link 636, a transmission or file type field 638, a submission reason field 640, a submission timeframe 642, and a case field or link 644. The name field or link 632 is a selectable and/or editable field or link that indicates a name of the submission representation 632 (e.g., to specify each). Likewise, the destination field or link 636 is a selectable and/or editable field or link that indicates or represents the submission address of the submission. For example, in FIG. 6B, the submissions section 628 includes a submission representation 632 being provided to the EMA (e.g., at the EMA health agency computing system 112), a submission representation 632 being provided to the FDA (e.g., at the FDA health agency computing system 112), and a submission representation 632 being provided to Health Canada (e.g., at the Health Canada health agency computing system 112).

The transmission or file type field 638 may represent or indicate the transmission type of the submission representation 632, which may be based on the submission address if the submission. For example, in FIG. 6B, the submissions section 628 includes a submission representation 632 with an EMA E2B(R2) XML file type, a submission representation 632 with an FDA E2B(R2) XML file type, and a submission representation 632 with a Health Canada E2B (R2) XML file type. Similarly, the submission reason field 640 may represent or indicate the reason for the submission being automatically generated, such as the initial submission to health authorities (e.g., after the initial adverse event data has been received), a follow-up submission to health authorities (e.g., after follow-up adverse event data has been received), and the like.

The submission timeframe 642 may represent or indicate the submission timeframe of the submission associated with the submission representation 632, which may be determined at step 332. Similarly, the case field or link 644 may represent or indicate the case dataset for which the submission is for. In some embodiments, the case field 644 is a link that, when selected, navigates the user computing device 108 to the case page 600 associated with the case dataset.

The process or submit submissions button 646 is selectable button that, when selected, provides an indication to the provider computing system 104 from the user computing device 108 to electronically transmit or output the case dataset for each of the submissions (e.g., associated with the submission representations 632). For example, in response to the selection of the submit submissions button 646, the user computing device 108 may send a submissions indication to the provider computing system 104. Then, in response to the provider computing system 104 receiving the submissions indication, the provider computing system 104 may electronically transmit the case dataset for each of the submission and to each of the submission addresses as the file type specified within the file type field 638. In other embodiments, the submit submissions button 646 is a selectable button that, when selected, provides an indication to provider computing system 104 from the user computing device 108 to generate the submissions and the submission timeframes (e.g., as described with regard to steps 332-336) based on the expectedness of the adverse event.

Referring now to FIG. 6C, the case overview section 650 provides the user of the user computing device 108 with an interface to manage and view an overview of the case dataset associated with the case page 600. As shown, the case overview section 650 includes a plurality of case fields 652, a listedness field 654, and an expectedness field 656.

The case fields 652 are texts fields through which the user of the user computing device 108 can view an overview of the case dataset such as the case number, the report type (e.g., study or marketed product), the receipt date, the date new case data was received, the associated study, the submission due date (as calculated based on the submission timeframe), the associated adverse event term and/or code, the seriousness, the relatedness, and the like. In this regard, each of the case fields 652 should be understood as including adverse event data and/or case data.

Like the case fields 652, the listedness field 654 is a text field through which the user of the user computing device 108 can view the listedness of the adverse event (e.g., as determined by the provider computing system 104 in the method 200 or 300 and provided to the user computing device 108). In some embodiments, the listedness of the adverse event is based on the IB or the company core data sheet.

Similarly, the expectedness field 656 is a text field through which the user of the user computing device 108 can view the expectedness of the adverse event (e.g., as determined by the provider computing system 104 in the method 200 or 300 and provided to the user computing device 108). In some embodiments, if any of the expectedness representations 612 indicate the adverse event is unexpected, the expectedness of the adverse event is unexpected. In other embodiments, if any of the expectedness representations 612 indicate the adverse event is expected, the expectedness of the adverse event is expected. In some embodiments, if the adverse event is associated with a study, the expectedness of the adverse event is based on the IB. In some embodiments, if the adverse event is not associated with a study, the expectedness of the adverse event is based on the company core data sheet and/or the region-specific reference documents.

The assessment section 660 provides the user of the user computing device 108 with an interface to manage assessments of the adverse event associated with the case dataset. As shown, the assessment section 660 includes a toggleable header 662 and one or more assessment representations 664. The toggleable header 662 may be similar or the same as the toggleable header 408.

Each assessment representations 664 represents or relates to an assessment of the adverse event. As shown, each assessment representations 664 includes a name field or link 666, a listedness field 668, an expectedness field 670, and an assessment tag 672. The name field or link 666 is a selectable and/or editable field or link that indicates a name of the assessment.

The listedness field 668 is a text field through which the user of the user computing device 108 can view the listedness of the adverse event (e.g., as determined by the provider computing system 104 in the method 200 or 300 and provided to the user computing device 108). Similarly, the expectedness field 670 is a text field through which the user of the user computing device 108 can view the expectedness of the adverse event (e.g., as determined by the provider computing system 104 in the method 200 or 300 and provided to the user computing device 108). Lastly, the assessment tag field 672 is a text field including shortened tag or acronym describing the adverse event (e.g., Suspected Unexpected Serious Adverse Reaction (SUSAR), Serious Adverse Event (SAE), etc.).

The embodiments described herein have been described with reference to the drawings. The drawings illustrate certain details of specific embodiments that implement the systems, methods, and programs described herein. However, describing the embodiments with drawings should not be construed as imposing on the disclosure any limitations that may be present in the drawings.

It should be understood that no claim element herein is to be construed under the provision of 35 U.S.C § 112(f), unless the element is expressly recited using the phrase "means for."

As used herein, the term "circuit" may include hardware structured to execute the functions described herein. In some embodiments, each respective "circuit" may include machine-readable media for configuring the hardware to execute the functions described herein. The circuit may be embodied as one or more circuitry components including, but not limited to, processing circuitry, network interfaces, peripheral devices, input devices, output devices, sensors, etc. In some embodiments, a circuit may take the form of one or more analog circuits, electronic circuits (e.g., integrated circuits (IC), discrete circuits, system on a chip (SOC) circuits), telecommunication circuits, hybrid circuits, and any other type of "circuit." In this regard, the "circuit" may include any type of component for accomplishing or facilitating achievement of the operations described herein. For example, a circuit as described herein may include one or more transistors, logic gates (e.g., NAND, AND, NOR, OR, XOR, NOT, XNOR), resistors, multiplexors, registers, capacitors, inductors, diodes, wiring, and so on.

The "circuit" may also include one or more processors communicably coupled to one or more memory or memory devices. In this regard, the one or more processors may execute instructions stored in the memory or may execute instructions otherwise accessible to the one or more processors. In some embodiments, the one or more processors may be embodied in various ways. The one or more processors may be constructed in a manner sufficient to perform at least the operations described herein. In some embodiments, the one or more processors may be shared by multiple circuits (e.g., circuit A and circuit B may comprise or otherwise share the same processor which, in some example embodiments, may execute instructions stored, or otherwise accessed, via different areas of memory). Alternatively or additionally, the one or more processors may be structured to perform or otherwise execute certain operations independent of one or more co-processors. In other embodiments, two or more processors may be coupled via a bus to enable independent, parallel, pipelined, or multi-threaded instruction execution. Each processor may be implemented as one or more general purpose processors, application specific integrated circuits (ASICs), field programmable gate arrays (FBGAs), digital signal processors (DSPs), or other suitable electronic data processing components structured to execute instructions provided by the memory. The one or more processors may take the form of a single core processor, a multi-core processor (e.g., dual core, quad core, etc.), micro-processor, etc. In some embodiments, the one or more processors may be external to the apparatus. For example, the one or more processors may be a remote processor (e.g., a cloud-based processor). Alternatively or additionally, the one or more processors may be internal and/or local to the apparatus. In this regard, a circuit or components thereof may be disposed locally (e.g., as part of a local server, a local computing system) or remotely (e.g., as part of a remote server such as a cloud-based server). To that end, a "circuit" as described herein may include components that are distributed across one or more locations. Further, the circuits of the processing circuit described herein may be distributed across one or more locations (e.g., each as part of one or more remote servers).

An example system for implementing the overall system or portions of the embodiments might include a general purpose computing device in the form of computers, including a processing unit, a system memory, and a system bus that couples various system components including the system memory to the processing unit. Each memory device may include non-transient volatile storage media, non-volatile storage media, non-transitory storage media (e.g., one or more volatile and/or non-volatile memories), etc. In some embodiments, the non-volatile storage media may take the form of ROM, flash memory (e.g., flash memory such as NAND, 3D NAND, NOR, 3D NOR), EEPROM, MRAM, magnetic storage, hard disks, optical disks, etc. Combinations of the above are also included within the scope of machine-readable media. In this regard, machine-executable instructions comprise, for example, instructions and data which cause a general purpose computer, special purpose computer, or special purpose processing machine to perform a certain function or group of functions. Each respective memory device may be operable to maintain or otherwise store data relating to the operations performed by one or more associated circuits, including processor instructions and related data (e.g., database components, object code components, script components), in accordance with the example embodiments described herein.

It should also be noted that the term "input devices," as described herein, may include any type of input device including, but not limited to, a keyboard, a keypad, a mouse, a joystick, or other input devices performing a similar function. Comparatively, the term "output device," as described herein, may include any type of output device including, but not limited to, a computer monitor, printer, facsimile machine, or other output devices performing a similar function.

It should be noted that although the diagrams herein may show a specific order and composition of method steps, it is understood that the order of these steps may differ from what is depicted. For example, two or more steps may be performed concurrently or with partial concurrence. Also, some method steps that are performed as discrete steps may be combined, steps being performed as a combined step may be separated into discrete steps, the sequence of certain processes may be reversed or otherwise varied. The order or sequence of any element or apparatus may be varied or substituted according to alternative embodiments. Accordingly, all such modifications are intended to be included within the scope of the present disclosure as defined in the appended claims. Such variations will depend on the machine-readable media and hardware systems chosen and on designer choice. It is understood that all such variations are within the scope of the disclosure. Likewise, software and web implementations of the present disclosure could be accomplished with standard programming techniques with rule-based logic and other logic to accomplish the various database searching steps, correlation steps, comparison steps, and decision steps.

The foregoing description of embodiments has been presented for purposes of illustration and description. It is not intended to be exhaustive or to limit the disclosure to the precise form disclosed, and modifications and variations are possible in light of the above teachings or may be acquired from this disclosure. The embodiments were chosen and described in order to explain the principles of the disclosure and its practical application to enable one skilled in the art to utilize the various embodiments and with various modifications as are suited to the particular use contemplated. Other substitutions, modifications, changes, and omissions may be made in the design, operating conditions and embodiment of the embodiments without departing from the scope of the present disclosure as expressed in the appended claim.

What is claimed is:

1. A method for determining and indicating expectedness of an adverse event in an expectedness monitoring and analyzation system, wherein the expectedness monitoring and analyzation system comprises a provider computing system and a user computing device communicating with each other via a network, and wherein the provider computing system comprises a document repository for storing electronic reference documents, the method comprising:

receiving, by a network interface of the provider computing system, adverse event data including a first medical dictionary for regulatory activities (MedDRA) code associated with the adverse event and a clinical study;

determining, by a processing circuit of the provider computing system, an electronic reference document associated with the clinical study;

selecting, by the processing circuit, the electronic reference document including a defined adverse reaction from the document repository, wherein the defined adverse reaction includes an active start date, a second MedDRA code, and a seriousness exclusion, and wherein the document repository enforces a system-wide single data source policy by maintaining a single version of the electronic reference document for the clinical study;

generating, by the processing circuit, a case dataset including at least a portion of the adverse event data;

determining, by the processing circuit, the expectedness of the adverse event based on the defined adverse reaction of the electronic reference document and the adverse event data;

determining, by the processing circuit, a first submission address associated with a first health agency, wherein the first health agency is the Food and Drug Agency (FDA), and wherein the first submission address is an address associated with the Electronics Submission Gateway (ESG) of the FDA;

determining, by the processing circuit, a second submission address associated with a second health agency;

determining, by the processing circuit, a first submission timeframe associated with the case dataset based on the expectedness of the adverse event and the first submission address;

determining, by the processing circuit, a second submission timeframe associated with the case dataset based on the expectedness of the adverse event and the second submission address, determining, by the processing circuit, a first submission comprising an E2B XML file type and the first submission address based on the adverse event data; and outputting, by AS2 gateway logic of the network interface, the case dataset as the E2B XML file type to the first submission address based on the first submission.

2. The method of claim 1, wherein the case dataset is output within the first submission timeframe.

3. The method of claim 1, further comprising:

determining, by the processing circuit, a second submission comprising a second file type and the second submission address based on the adverse event data;

and outputting, by the network interface, the case dataset as the second file type to the second submission address based on the second submission.

4. The method of claim 1, wherein the adverse event data includes seriousness data, and wherein the first submission timeframe is determined based on the expectedness of the adverse event, the first submission address, and the seriousness data.

5. The method of claim 1, wherein determining the expectedness of the adverse event comprises:

determining, by the processing circuit, the first MedDRA code of the adverse event matches the second MedDRA code of the defined adverse reaction; and determining, in response to the date data being after the active start date of the defined adverse reaction and by the processing circuit, the adverse event is unexpected.

6. The method of claim 1, wherein the seriousness exclusion identifies a seriousness of the adverse event for which the adverse event is expected or unexpected.

7. The method of claim 1, wherein the adverse event data includes seriousness data and date data, and wherein determining the expectedness for the adverse event comprises:

determining, in response to the date data being after the active start date of the defined adverse reaction and by the processing circuit, the seriousness exclusion of the electronic reference document at least partially matches the seriousness data; and determining, by the processing circuit, the adverse event is unexpected based on the seriousness exclusion at least partially matching the seriousness data.

8. The method of claim 1, further comprising:

indicating, by the processing circuit, the expectedness of the adverse event in the case dataset; and providing, by the network interface, at least a portion of the case dataset to the user computing device to enable display on a user interface, wherein the user interface includes an expectedness section including the indication of the expectedness of the adverse event.

9. The method of claim 1, further comprising:

providing, by the network interface, at least a portion of the electronic reference document to the user computing device to enable display on a user interface, wherein the user interface includes a defined adverse reactions section;

receiving, by the network interface, the defined adverse reaction from the user computing device including the active start date, wherein the defined adverse reaction is received via the defined adverse reactions section of the user interface; and storing, by the document repository, the defined adverse reaction in association with the electronic reference document.

10. The method of claim 9, wherein the user interface includes a seriousness exclusion drop-down box, and further comprising:

receiving, by the network interface, the seriousness exclusion from the user computing device, wherein the seriousness exclusion is received via the seriousness exclusion drop-down box of the user interface; and storing, by the document repository, the seriousness exclusion in association with the electronic reference document.

11. A method for determining and indicating expectedness of a first adverse event and a second adverse event in an expectedness monitoring and analyzation system, wherein the expectedness monitoring and analyzation system comprises a provider computing system including a document repository for storing electronic reference documents, the method comprising:

receiving, by a network interface of the provider computing system, adverse event data associated with medical product and including a first medical dictionary for regulatory activities (MedDRA) code associated with the first adverse event and a second MedDRA code associated with the second adverse event;

determining, by a processing circuit of the provider computing system, an electronic reference document associated with the medical product;

selecting, by the processing circuit, the electronic reference document including a plurality of defined adverse reactions from the document repository, wherein each defined adverse reaction of the plurality of defined adverse reactions includes an active start date, at least one MedDRA code, and a seriousness exclusion, and wherein the document repository enforces a system-wide single data source policy by maintaining a single version of the electronic reference document for the medical product;

generating, by the processing circuit, a first case dataset including at least a first portion of the adverse event data;

generating, by the processing circuit, a second case dataset including at least a second portion of the adverse event data;

determining, by the processing circuit, the expectedness of the first adverse event based on a first defined adverse reaction of the plurality of defined adverse reactions and the adverse event data;

determining, by the processing circuit, the expectedness of the second adverse event based on a second defined adverse reaction of the plurality of defined adverse reactions and the adverse event data;

determining, by the processing circuit, a first submission address associated with a first health agency, wherein the first health agency is the Food and Drug Agency (FDA), and wherein the first submission address is an address associated with the Electronics Submission Gateway (ESG) of the FDA;

determining, by the processing circuit, a second submission address associated with a second health agency;

determining, by the processing circuit, a first submission timeframe associated with the first case dataset based on the expectedness of the first adverse event and at least one: of the first submission address or the second submission address;

determining, by the processing circuit, a second submission timeframe associated with the second case dataset based on the expectedness of the second adverse event and at least one of: the first submission address or the second submission address;

determining, by the processing circuit, a first submission comprising an E2B XML file type and the first submission address based on the adverse event data; and outputting, by AS2 gateway logic of the network interface, the case dataset as the E2B XML file type to the first submission address based on the first submission.

12. The method of claim 11, wherein the first case dataset is output within the first submission timeframe, and wherein the method further comprises:

outputting, by the network interface, the second case dataset within the second submission timeframe.

13. The method of claim 11, further comprising:

determining, by the processing circuit, a second submission associated with the second case dataset comprising a second file type and the second submission address based on the adverse event data;

outputting, by the network interface, the second case dataset as the second file type to the second submission address based on the second submission.

14. The method of claim 11, wherein the adverse event data includes seriousness data, and wherein the first submission timeframe is determined based on the expectedness of the first adverse event, the at least one: of the first submission address or the second submission address, and the seriousness data.

15. The method of claim 11, wherein determining the expectedness for the first adverse event comprises:

determining, by the processing circuit, the first MedDRA code associated with the first adverse event matches the at least one MedDRA code of the first defined adverse reaction; and determining, in response to the date data being after the active start date of the first defined adverse reaction and by the processing circuit, the first adverse event is expected.

16. The method of claim 11, wherein the adverse event data includes seriousness data and date data, and wherein determining the expectedness of the second adverse event comprises:

determining, in response to the date data being after the active start date of the second defined adverse reaction and by the processing circuit, the seriousness exclusion of the electronic reference document at least partially matches the seriousness data; and determining, by the processing circuit, the second adverse event is unexpected based on the seriousness exclusion at least partially matching the seriousness data.

17. The method of claim 11, wherein each seriousness exclusion identifies a seriousness of each adverse event for which each adverse event is expected or unexpected.

18. The method of claim 11, further comprising:

indicating, by the processing circuit, the expectedness of the first adverse event in the first case dataset; and providing, by the network interface, at least a portion of the first case dataset to the user computing device to enable display on a user interface, wherein the user interface includes an expectedness section including the indication of the expectedness of the first adverse event.

19. The method of claim 11, further comprising:

providing, by the network interface, at least a portion of the electronic reference document to the user computing device to enable display on a user interface, wherein the user interface includes a defined adverse reactions section;

receiving, by the network interface, the first defined adverse reaction from the user computing device including the active start date, wherein the first defined adverse reaction is received via the defined adverse reactions section of the user interface; and storing, by the document repository, the first defined adverse reaction in association with the electronic reference document.

20. The method of claim 19, wherein the user interface includes a seriousness exclusion drop-down box and further comprising:

receiving, by the network interface, the seriousness exclusion of the first adverse reaction from the user computing device, wherein the seriousness exclusion of the first adverse reaction is received via the seriousness exclusion drop-down box of the user interface; and storing, by the document repository, the seriousness exclusion of the first adverse reaction in association with the electronic reference document.

* * * * *